United States Patent [19]

Osborn, III

[11] Patent Number: 5,733,274
[45] Date of Patent: Mar. 31, 1998

[54] SANITARY NAPKIN HAVING STIFFENED CENTER

[75] Inventor: Thomas Ward Osborn, III, Cincinnati, Ohio

[73] Assignee: The Procter & Gamble Company, Cincinnati, Ohio

[21] Appl. No.: 707,914

[22] Filed: Sep. 10, 1996

Related U.S. Application Data

[63] Continuation of Ser. No. 509,614, Jul. 31, 1995, abandoned, which is a continuation of Ser. No. 204,794, Mar. 2, 1994, abandoned, which is a continuation of Ser. No. 823,797, Jan. 22, 1992, abandoned, which is a division of Ser. No. 605,583, Oct. 29, 1990, abandoned, and a continuation-in-part of Ser. No. 960,176, Oct. 8, 1992, Pat. No. 5,383,869, which is a continuation of Ser. No. 688,755, Apr. 22, 1991, abandoned, which is a continuation of Ser. No. 570,231, Aug. 20, 1990, Pat. No. 5,009,653, which is a continuation of Ser. No. 293,606, Jan. 4, 1989, Pat. No. 4,950,264, which is a continuation-in-part of Ser. No. 175,559, Mar. 31, 1988, abandoned.

[51] Int. Cl.$^6$ .............................. A61F 13/15; A61F 13/20
[52] U.S. Cl. ........................ 604/385.1; 604/358; 604/378
[58] Field of Search ............................ 604/358, 366–370, 604/378, 385.1

[56] References Cited

U.S. PATENT DOCUMENTS

| | | | |
|---|---|---|---|
| 810,127 | 1/1906 | Green | 604/378 |
| 810,131 | 1/1906 | Green | 604/378 |
| 1,959,282 | 5/1934 | Bade . | |
| 1,974,578 | 9/1934 | Medoff . | |
| 2,064,431 | 12/1936 | Jurgensen . | |
| 2,331,355 | 10/1943 | Strongson . | |
| 2,662,527 | 12/1953 | Jacks . | |
| 2,747,575 | 5/1956 | Mercer . | |
| 3,084,692 | 4/1963 | Atkinson . | |
| 3,294,091 | 12/1966 | Morse . | |
| 3,406,689 | 10/1968 | Hicks et al. . | |
| 3,528,422 | 9/1970 | Hodas . | |
| 3,570,493 | 3/1971 | Olsson . | |
| 3,575,174 | 4/1971 | Mogor . | |
| 3,604,423 | 9/1971 | Fraser . | |
| 3,654,929 | 4/1972 | Nilsson et al. . | |
| 3,731,688 | 5/1973 | Litt et al. . | |
| 3,805,790 | 4/1974 | Kaczmarzyk et al. . | |
| 3,814,100 | 6/1974 | Nystrand . | |
| 3,863,637 | 2/1975 | MacDonald et al. . | |
| 3,865,112 | 2/1975 | Roeder . | |
| 3,926,189 | 12/1975 | Taylor . | |
| 3,951,150 | 4/1976 | Schaar . | |
| 3,954,107 | 5/1976 | Chesky et al. . | |
| 3,995,640 | 12/1976 | Schaar . | |
| 4,014,338 | 3/1977 | Schaar . | |

(List continued on next page.)

FOREIGN PATENT DOCUMENTS

| | | |
|---|---|---|
| 0 336 578 | 10/1989 | European Pat. Off. . |
| 0 471 114 A2 | 1/1991 | European Pat. Off. . |
| 2 168 612 | 6/1986 | United Kingdom . |
| 2191098 | 12/1987 | United Kingdom . |
| WO 88/04547 | 6/1988 | WIPO . |

*Primary Examiner*—P. Zuttarelli
*Attorney, Agent, or Firm*—Jeffrey V. Bamber; Steven W. Miller; Jacobus C. Rasser

[57] ABSTRACT

A disposable absorbent article, such as a sanitary napkin, is disclosed that has components which may separate in the Z-direction with relation to other components of the article when the absorbent article is worn. The sanitary napkin of the present invention comprises a liquid pervious topsheet, a liquid impervious backsheet, an absorbent core positioned between the topsheet and the backsheet, and a relatively shift liquid pervious spacing structure for moving the topsheet away from the core. The spacing structure is generally positioned between the topsheet and the core. The spacing structure has a longitudinal centerline, and opposed lateral sides which may move inwardly toward the longitudinal centerline when the spacing is compressed from the sides. This results in at least a portion of the spacing structure moving the topsheet apart from the absorbent core. In an alternative embodiment, the sanitary napkin of the present invention also has an absorbent core which separates from the backsheet of the sanitary napkin.

8 Claims, 8 Drawing Sheets

U.S. PATENT DOCUMENTS

| | | |
|---|---|---|
| 4,029,101 | 6/1977 | Chesky et al. . |
| 4,067,336 | 1/1978 | Johnson . |
| 4,079,739 | 3/1978 | Whitehead . |
| 4,182,334 | 1/1980 | Johnson . |
| 4,195,634 | 4/1980 | Di Salvo et al. ............... 604/385.1 |
| 4,217,901 | 8/1980 | Bradstreet et al. ............... 604/368 |
| 4,338,939 | 7/1982 | Daville . |
| 4,340,058 | 7/1982 | Pierce et al. . |
| 4,405,326 | 9/1983 | Lenaghan . |
| 4,425,130 | 1/1984 | DesMarais . |
| 4,505,705 | 3/1985 | Matthews et al. . |
| 4,505,706 | 3/1985 | Erpicum et al. . |
| 4,551,142 | 11/1985 | Kopolow ............... 604/379 |
| 4,554,191 | 11/1985 | Korpman . |
| 4,560,379 | 12/1985 | Stemmler . |
| 4,576,596 | 3/1986 | Jackson et al. . |
| 4,595,392 | 6/1986 | Johnson et al. . |
| 4,605,405 | 8/1986 | Lassen . |
| 4,609,373 | 9/1986 | Johnson . |
| 4,627,848 | 12/1986 | Lassen et al. . |
| 4,631,062 | 12/1986 | Lassen et al. . |
| 4,654,040 | 3/1987 | Luceri . |
| 4,655,759 | 4/1987 | Romans-Hess et al. . |
| 4,662,877 | 5/1987 | Williams . |
| 4,666,440 | 5/1987 | Malfitano . |
| 4,673,403 | 6/1987 | Lassen et al. . |
| 4,681,577 | 7/1987 | Stern et al. . |
| 4,685,914 | 8/1987 | Holtman . |
| 4,687,478 | 8/1987 | Van Tilburg . |
| 4,701,177 | 10/1987 | Ellis et al. . |
| 4,787,896 | 11/1988 | Houghton et al. . |
| 4,790,839 | 12/1988 | Ahr . |
| 4,804,380 | 2/1989 | Lassen et al. . |
| 4,846,824 | 7/1989 | Lassen et al. . |
| 4,944,735 | 7/1990 | Mokry . |
| 4,950,264 | 8/1990 | Osborn, III ............... 604/385.1 |
| 5,037,418 | 8/1991 | Kons et al. . |
| 5,248,309 | 9/1993 | Serbiak et al. . |
| 5,575,786 | 11/1996 | Osborn, III . |

SANITARY NAPKIN HAVING STIFFENED CENTER

CROSS-REFERENCE TO RELATED APPLICATIONS

This is a continuation of Ser. No. 08/509,614 filed on Jul. 31, 1995 (abandoned) which is a continuation application of Ser. No. 08/204,794 filed Mar. 2, 1994 (abandoned), which is a continuation of Ser. No. 07/823,797 filed Jan. 22, 1992 (abandoned) which is a divisional of Ser. No. 07/605,583 filed Oct. 29, 1990 (abandoned); and a continuation-in-part of Ser. No. 07/960,176 filed Oct. 8, 1992 (now U.S. Pat. No. 5,383,869), which is a continuation of Ser. No. 07/688,755 filed Apr. 22, 1991 (abandoned), which is a continuation of Ser. No. 07/570,231 filed Aug. 20, 1990 (now U.S. Pat. No. 5,009,653), which is a continuation of Ser. No. 07/293,606 filed Jan. 4, 1989 (now U.S. Pat. No. 4,950,264), which is a continuation-in-part of Ser. No. 175,559 filed Mar. 31, 1988 (abandoned).

FIELD OF THE INVENTION

The present invention relates generally to disposable absorbent articles such as sanitary napkins worn by women, and more particularly to sanitary napkins that have components capable of separation in use to provide improved contact of the sanitary napkin with the wearer's body and increased protection from soiling of the wearer's undergarments.

BACKGROUND OF THE INVENTION

Absorbent articles such as sanitary napkins, pantiliners, and incontinent pads are designed to absorb and retain liquid and other discharges from the human body and to prevent body and clothing soiling. It has been found to be desirable to attempt to create absorbent articles, such as sanitary napkins, that maintain contact with the body of the wearer when they are worn. It is even more desirable that sanitary napkins also conform as closely as possible to the body of the wearer. Such a body-conforming capability is believed to increase the effectiveness of the sanitary napkin by reducing the possibility that menses will travel around the perimeter of the sanitary napkin and leak.

There have been a number of recent efforts to provide sanitary napkins and other absorbent articles with improved body-conforming characteristics. Two recent efforts are described in U.S. Pat. No. 4,950,264, issued to Osborn, III, on Aug. 21, 1990, and U.S. patent application Ser. No. 07/175,817, entitled "Absorbent Article" filed Mar. 31, 1988 in the name of Kenneth Barclay Buell, both of which are incorporated by reference herein. While the sanitary napkins disclosed in these references work quite well, the search for new and different ways of improving body contact has continued.

It is especially desirable that sanitary napkins maintain contact with and conform to the body of the wearer under dynamic conditions (when the wearer walks, sits, etc.). There are certain critical dynamic conditions which stress the sanitary napkin and tend to reduce its ability to stay in contact with the body of the wearer. As soon as the sanitary napkin is put on, for instance, the sanitary napkin is subjected to lateral compression by the upper portions of the wearer's thighs. The forces applied by the wearer's thighs generally tend to distort the shape of the sanitary napkin, reducing the size of the target the sanitary napkin provides.

One attempt to control the effect of these compressive forces is disclosed in UK Patent Application 2 168 612 A, published Jun. 25, 1986. The UK patent application discloses a sanitary towel with a resilient insert positioned within the core or adjacent to a face of the core that is intended to inhibit permanent distortion of the towel. The insert only serves to resist deformation of the sanitary towel, however, it does not utilize the compressive forces to improve contact of the towel with the wearer's body. Further, the UK patent application does not teach or disclose utilizing the compressive forces to provide the sanitary towel with body-conforming properties.

In addition, as is well known, sanitary napkins are generally fastened to the wearer's undergarments by a pressure sensitive adhesive or other means. The means is stressed when the wearer moves about, because the wearer's undergarments may not move in concert with the body of the wearer, and the sanitary napkin may not flex and twist with the wearer's undergarments. If stressed excessively, the pressure sensitive adhesive, or other means may become detached from the undergarment. This will cause the sanitary napkin to shift from the desired position and registration with the wearer's vaginal opening. It is, therefore, also desirable to provide the body-conforming sanitary napkin with a mechanism to accomodate the independence of movement between the body of the wearer and the wearer's undergarments.

It is, therefore, an object of this invention to provide an absorbent article, such as a sanitary napkin, which readily intercepts menses when discharged by maintaining contact with and conforming to the shape of the female urogenital and buttocks region.

It is also an object of this invention to provide a sanitary napkin which maintains contact with the wearer throughout the range of normal movements encountered while the sanitary napkin is worn. It is also desirable that the sanitary napkin continue to maintain contact with the wearer's body when it is subjected to the forces that normally accompany the wearing of a sanitary napkin.

It is another object of the present invention to provide a sanitary napkin that advantageously utilizes the compressive forces exerted by the wearer's thighs to improve the contact between the sanitary napkin and the wearer's body.

It is another object of the present invention to provide a sanitary napkin that has body-contacting and body-conforming components that do not have any sharp corners, edges, or fold lines that would irritate the wearer.

Finally, it is an object of this invention to provide a sanitary napkin with a mechanism to accomodate the independence of movement between the body of the wearer and the wearer's undergarments.

These and other objects of the present invention will be more readily apparent when considered in reference to the following description and when taken in conjunction with the accompanying drawings.

SUMMARY OF THE INVENTION

The present invention is an absorbent article, such as a sanitary napkin. The sanitary napkin of the present invention has components which may move apart from other components of the sanitary napkin when the sanitary napkin is worn. In particular, the sanitary napkin has a topsheet that may be moved away from the absorbent core of the sanitary napkin to contact and conform with the wearer's body.

The sanitary napkin of the present invention comprises at least four primary components. These are a liquid pervious topsheet, a liquid impervious backsheet, an absorbent core positioned between the topsheet and the backsheet, and a liquid pervious spacing structure for moving the topsheet away from the core (the "spacing structure"). The spacing structure is generally positioned between the topsheet and the core.

The spacing structure can be an element of any shape (such as folded sheet) that is capable of spacing the topsheet away from the core when it is subjected to laterally compressive forces. The spacing structure has an uncompressed configuration, and a compressed configuration. The spacing structure is in its uncompressed configuration when it is not being subjected to any laterally compressive forces, such as those applied by the upper portions of the wearer's thighs when the sanitary napkin is worn. The spacing structure also has its own longitudinal and transverse axes. The spacing structure comprises several portions, including an upper portion, a lower portion, and opposed lateral sides. The upper portion of the spacing structure is positioned between the topsheet and the lower portion. The lower portion is adjacent to core when the spacing structure is in its uncompressed configuration. At least a section of the lower portion is connected to at least part of the core to define an attached section of the lower portion. The relationship between the upper portion and the lower portion is such that parts of the upper portion overlay parts of the lower portion when the spacing structure is in its uncompressed configuration. When the spacing structure is compressed from the sides, the opposed lateral sides may move inwardly toward the longitudinal centerline. This results in at least some of the upper portion moving the topsheet apart from the absorbent core.

In one embodiment, the sanitary napkin of the present invention also has an absorbent core that separates from the backsheet of the sanitary napkin. The separation of the absorbent core from the backsheet provides increased protection from soiling of the wearer's undergarments. This separation is made possible by virtue of the fact that the core is joined to the backsheet along the longitudinal edges of the sanitary napkin and along at least one transverse juncture. The remainder of the core is unattached to the backsheet so the unattached portion of the core may move apart from the backsheet. This embodiment of the sanitary napkin is also provided with a means for controlling the separation of the core from the backsheet.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

Figure 1:
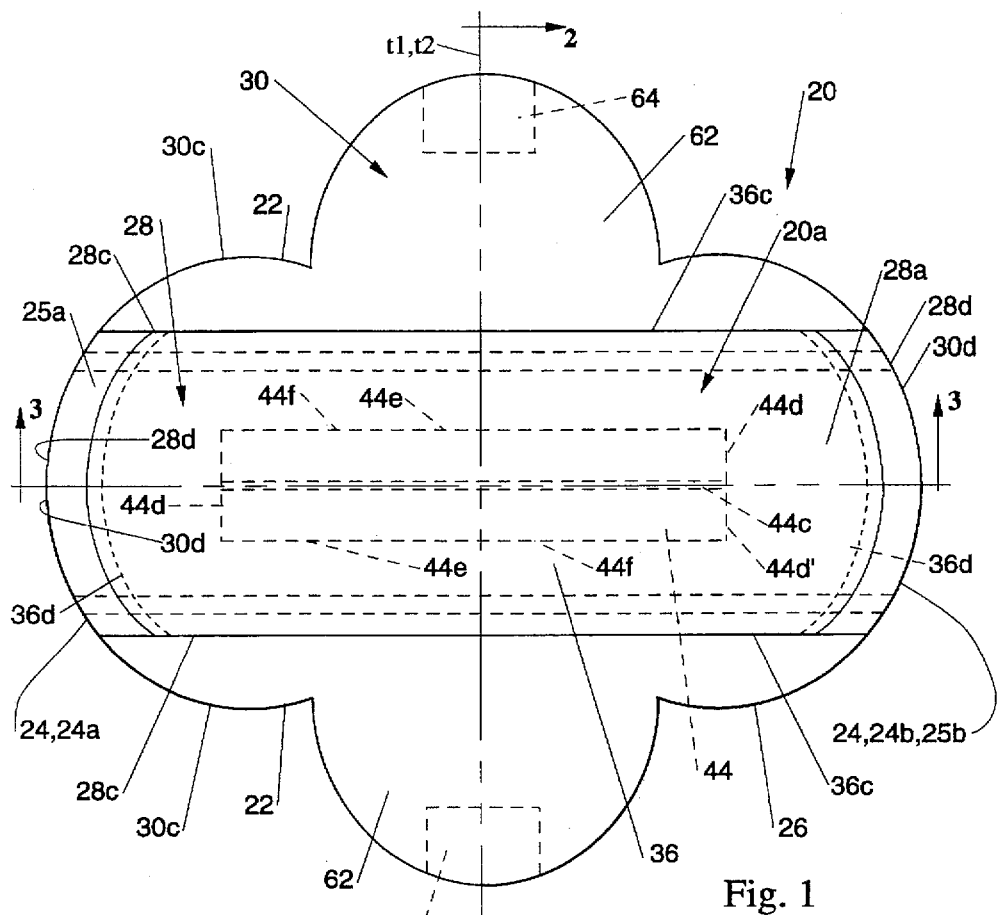
FIG. 1 is a top plan view of the sanitary napkin of the present invention.
Figure 2:
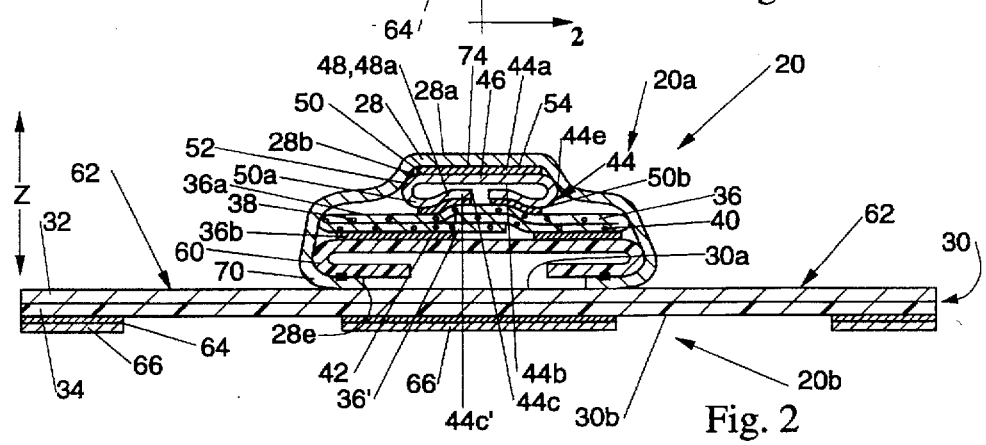
FIG. 2 is a section view taken along line 2—2 of FIG. 1 which shows the sanitary napkin of the present invention in its uncompressed configuration.
Figure 3:
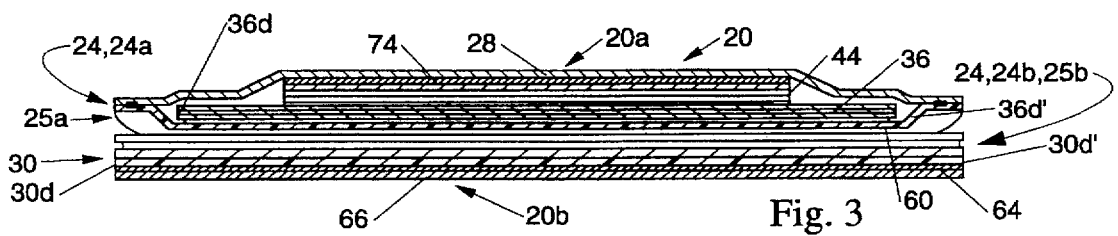
FIG. 3 is a section view taken along line 3—3 of FIG. 1 of the sanitary napkin in its uncompressed configuration.

Referring now to the drawings, a preferred embodiment of a disposable absorbent article of the present invention is shown in FIGS. 1–3.

As used herein, the term "absorbent article" refers to articles which absorb and contain body exudates. More specifically, the term refers to articles which are placed against or in proximity to the body of the wearer to absorb and contain the various exudates discharged from the body. The term "absorbent article" is intended to include sanitary napkins, pantiliners, and incontinent pads (articles worn in the crotch region of a garment). The term "disposable" refers to articles which are intended to be discarded after a single use. That is, disposable articles are not intended to be laundered or otherwise restored or reused). In the preferred embodiment illustrated, the absorbent article is a sanitary napkin designated 20.

1. Overall Characteristics of the Absorbent Article

The overall characteristics of the sanitary napkin 20 of the present invention will be discussed first.

The sanitary napkin 20 has two surfaces, a body surface 20a and a garment surface 20b. The sanitary napkin 20 is shown in FIG. 1 as viewed from its body surface 20a. The body surface 20a is intended to be worn adjacent to the body of the wearer. The garment surface 20b of the sanitary napkin 20 (shown in FIG. 2) is on the opposite side and is intended to be placed adjacent to the wearer's undergarments when the sanitary napkin 20 is worn.

The sanitary napkin 20 has two centerlines, a principal longitudinal centerline $l_1$ and a principal transverse centerline $t_1$. As used herein the term "longitudinal" refers to a line, axis or direction in the plane of the sanitary napkin 20 that will be generally aligned with (e.g., approximately parallel to) a vertical plane which bisects a standing wearer into left and right body halves when the sanitary napkin 20 is worn. The term "transverse" refers to the line, axis or direction generally perpendicular to the longitudinal direction which lies within the plane of the sanitary napkin 20. The sanitary napkin 20 has a longitudinal dimension that runs in the general direction of the principal longitudinal centerline $l_1$, and a transverse dimension that runs in the general direction of the principal transverse centerline $t_1$. The sanitary napkin 20 is typically longer in the longitudinal dimension than in the transverse dimension.

FIG. 1 shows that the sanitary napkin 20 also has two spaced apart longitudinal edges 22 and two spaced apart transverse or end edges (or "ends") 24, which together form the periphery 26 of the sanitary napkin 20. When the sanitary napkin 20 is worn, one of the end edges 24 will be oriented toward the front of the wearer, and one of the end edges 24 will be oriented toward the rear of the wearer. The end edge 24 oriented toward the front of the wearer is designated 24a, and the end edge oriented toward the rear of the wearer is designated 24b.

The properties of the sanitary napkin 20 include its thickness, surface area, and its flexibility. The sanitary napkin 20 can be of any thickness, including relatively thick or relatively thin. The embodiment of the sanitary napkin 20 shown in the drawings is intended to be an example of a relatively thin sanitary napkin 20. It should be understood, however, when viewing the drawings that the number of layers of material shown cause the sanitary napkin 20 to appear much thicker than it actually is. A "thin" sanitary napkin 20 will generally have a caliper of less than about 10 millimeters. Still, some thin sanitary napkins have a caliper of less than about 7 millimeters. The above calipers are to be measured with a comparator gauge having a test weight of approximately 80.0 grams. The comparator gauge should have a comparator foot that weighs approximately 10 grams and has a diameter of about 2.54 centimeters. The comparator gauge should have a contact surface area of approximately 5.1 square centimeters. The surface area of the topsheet 28 of the sanitary napkin 20 of the present invention should be at least about 100 square centimeters. This will prevent discharged fluids from missing the target that the sanitary napkin 20 provides. The sanitary napkin 20 should also be preferably relatively flexible, so that it is comfortable for the wearer.

FIG. 2 shows the individual components of the sanitary napkin 20. The sanitary napkin 20 of the present invention generally comprises four primary components. These include a liquid pervious topsheet 28, a liquid impervious backsheet (or "barrier means") 30, an absorbent core 36, and a liquid pervious spacing structure for moving the topsheet away from the absorbent core (the "spacing structure") 44. The absorbent core 36 is positioned between the topsheet 28 and the backsheet 30. The spacing structure 44 is positioned between the topsheet 28 and the absorbent core 36 in the embodiment shown in FIG. 2. As shown in FIG. 2, the spacing structure 44 has several portions. These include an upper portion 46, a lower portion 48, and opposed lateral sides 52. The components of the sanitary napkin 20 and the portions of the spacing structure 44 are described in greater detail below.

Figure 6:
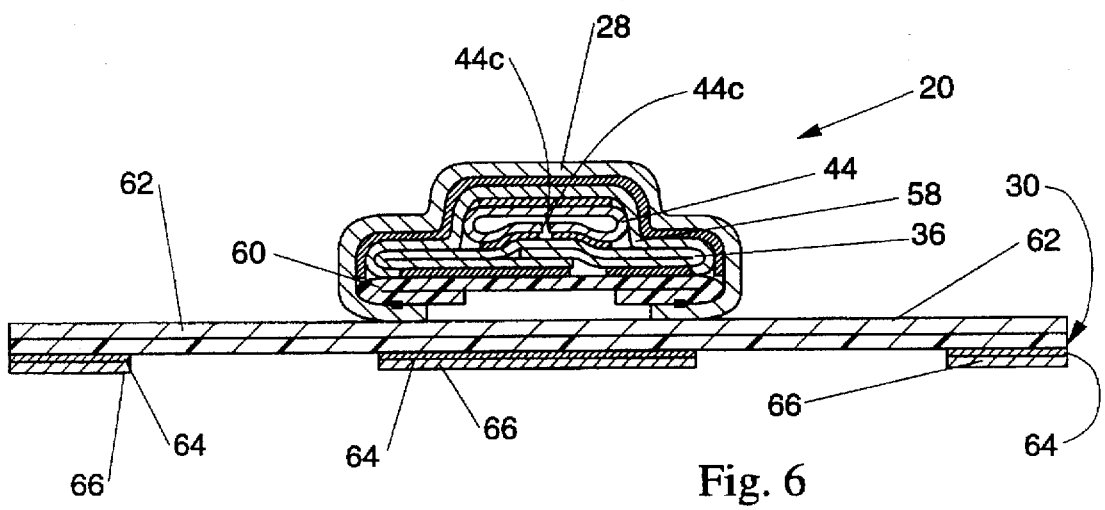
FIG. 6 shows an alternative version of the sanitary napkin of the present invention in which a pervious material is placed between the topsheet and the spacing structure.

The sanitary napkin 20 of the present invention can also be provided with any optional additional components that are known in the art. The optional components may include one or more wicking layers 58 (such as is shown in FIG. 6), an optional interliner 60 (FIG. 2), side flaps 62 (FIGS. 1 and 2), an adhesive fastening means 64 (FIG. 2), and a removable cover strip or release liner 66 (FIG. 2). In the embodiment shown in FIG. 6, the sanitary napkin 20 of the present invention is provided with a wicking layer 58 positioned between the topsheet 28 and the absorbent core 36. As shown in FIG. 2, the optional interliner 60 is positioned between the absorbent core 36 and the backsheet 30. The sanitary napkin 20 may be provided with side flaps or "wings" 62 that are folded around the crotch portion of the wearer's panties. (The wearer's panties or undergarments are designated U in the drawings.) The adhesive fastening means 64 serves as a means for attaching the sanitary napkin 20 to the undergarment of the wearer. The removable release liner 66 covers the adhesive fastening means 64 in order to keep the adhesive from drying out or sticking to a surface other than the crotch portion of the undergarment prior to use. (These optional components are also described in greater detail below.)

The key features of the sanitary napkin 20 of the present invention include the fact that the sanitary napkin 20 has certain components which may move apart from other components of the sanitary napkin. The movement of some components apart from other components of the sanitary napkin 20 is also referred to as the "decoupling of", or "separation from" the other components. In addition, not only may some components move apart, there may be separation of more than one set of components in the sanitary napkin 20 of the present invention. This separation of multiple components may be referred to as "compound decoupling" for short. In one embodiment, there is separation of at least two sets of components of the sanitary napkin 20. The separation of two sets of components is referred to as "dual" or "double" decoupling for short.

The first set of components that may move apart comprises the topsheet 28 and the absorbent core 36. In the case of the first set of components, when the sanitary napkin 20 is worn, at least a portion of the topsheet 28 may be moved apart from the absorbent core 36 by the spacing structure 44. The second set of components comprises the absorbent core 36 and the backsheet 30. The separation of the second set of components is optional. The separation of the components provides the sanitary napkin 20 with improved contact with the wearer's body and increased protection from soiling of the wearer's undergarments.

Several matters should be understood with reference to the decoupling of the components of the sanitary napkin 20.

The separation or decoupling of the components refers to a movement of one component apart from another in a direction generally perpendicular to the principal longitudinal and transverse axes of the sanitary napkin (that is, in the "Z-direction"). The "Z-direction" is an orientation with respect to the sanitary napkin 20 of the present invention if the sanitary napkin 20 is placed in a Cartesian coordinate system in its flat, laid out condition of FIG. 1 so that the garment side 20b of the sanitary napkin 20 lies in the plane formed by the x and y axes. The principal longitudinal and transverse centerlines $l_1$ and $t_1$ of the sanitary napkin 20 lie in the plane formed by the x and y axes. The "Z-direction" is the direction that is perpendicular to the plane of either surface of the sanitary napkin 20 when it is in such a flat, laid out configuration.

The second matter relates to the nature of the separation of the components. Typically, as used herein, the moving of the components apart, or the "decoupling" of the components refers to a situation in which portions of the components are joined or attached (and the remaining portions are unattached) before, during and after decoupling. The unattached portions move apart during the decoupling, while the attached portions remain joined together. The moving of the components apart may alternatively refer to a situation in which the attached portions of the components partially or completely separate with the unattached portions. Both types of decoupling are intended to be within the scope of the present invention.

A third matter relates to when separation occurs, and to the amount of separation. The components of the sanitary napkin 20 need only be capable of separation. The present invention is, thus, not limited to sanitary napkins having components that will separate in all cases and under all conditions. There may be certain circumstances in which the components of the sanitary napkin 20 will remain in contact with each other. The components must only separate enough for the sanitary napkin 20 to be operable. Preferably, the components that are capable of separating will in fact separate when the sanitary napkin 20 is worn.

In the following sections of this description, the characteristics of the components of the sanitary napkin 20 are discussed in greater detail (Section 2). The separation of the topsheet 28 from the absorbent core 36 is discussed in Section 3 in conjunction with the spacing structure 44. The optional components are discussed in Section 4. The separation of the absorbent core 36 from the backsheet 30 is discussed in Section 5. In addition to the description provided below, it should also be understood that the sanitary napkin 20 of the present invention could be constructed in accordance with U.S. Pat. No. 4,950,264, issued to Osborn on Aug. 21, 1990, previously incorporated by reference herein, which patent fully sets forth the flexure-resistance of the sanitary napkin described therein, and a method of measuring the same.

2. The Individual Components of the Absorbent Article

Looking at the components of the sanitary napkin 20 more specifically, FIG. 2 shows the liquid pervious topsheet (or simply the "topsheet") 28 overlies, and is folded around several of the other components of the sanitary napkin 20. The topsheet 28 is oriented towards and contacts the body of the wearer. The topsheet 28 is the portion of the sanitary napkin 20 that initially receives bodily discharges. The topsheet 28 has a body-facing side (or "body surface") 28a and a core-facing side 28b. The body-facing side 28a of the topsheet 28 generally forms at least a portion of the body surface 20a of the sanitary napkin 20. FIG. 1 shows that the topsheet 28 has two longitudinal edges 28c and two end edges 28d.

The topsheet 28 should permit liquids to readily transfer through its thickness toward the absorbent core 36. The topsheet 28 should, therefore, be liquid pervious. The topsheet 28 should also be flexible and nonirritating to the wearer's skin. As used herein the term "flexible" refers to materials which are compliant and readily conform to the shape of the body or respond by easily deforming in the presence of external forces. Preferably the topsheet 28 is not noisy, to provide discretion for the wearer. The topsheet 28 should be clean in appearance and somewhat opaque to hide the bodily discharges collected in and absorbed by the core 36. The topsheet 28 should further exhibit good strikethrough and a reduced tendency to rewet, permitting bodily discharges to rapidly penetrate the topsheet 28 to the core 36, but not allowing such discharges to flow back through the topsheet 28 to the skin of the wearer.

The topsheet 28 preferably also has a plurality of apertures to permit liquids deposited thereon to pass through to the core 36. Such apertures may, but need not, also be present in any extension of the topsheet 28 that may comprise a portion of the flaps 62. If apertured, the topsheet 28 should have about 5 to about 60 percent open area, preferably, about 25 percent, and a thickness of about 0.01 to about 0.05 millimeters. If desired, the topsheet 28 may be sprayed with a surfactant to enhance fluid penetration to the core 36. The surfactant should typically be nonionic and should be nonirritating to the skin. A surfactant density of about 0.01 milligrams per square centimeter of topsheet 28 area is suitable. A suitable surfactant is sold by the Glyco Chemical, Inc. of Greenwich, Conn., as Pegosperse 200 ML. The topsheet 28 may also have absorbent capacity if the core 36 has a capillary system or a Z-direction system of fibers.

A suitable topsheet 28 may be made from a number of different materials, such as nonwoven materials and perforated polyolefinic films. The topsheet 28 may be manufactured by any suitable process. A particularly suitable topsheet 28 may be made in accordance with U.S. Pat. No. 4,342,314 issued Aug. 3, 1982 to Radel et al. and U.S. Pat. No. 4,463,045 issued Jul. 31, 1984 to Ahr et al., which patents are incorporated herein by reference. An elastically inextensible topsheet 28 made of model X-3265 or model P1552 apertured formed film sold by the Ethyl Corporation, Visqueen Division, of Terre Haute, Ind. has also been found to work well in sanitary napkins.

The backsheet 30 is shown in FIG. 2. The backsheet 30 is the component of the sanitary napkin 20 that prevents the exudates from wetting articles which contact the sanitary napkin 20. Typically, the articles which come in contact with the sanitary napkin 20 would be the wearer's panties. The present invention is also concerned, however, with keeping the wearer's body and clothing free from soiling.

As shown in FIG. 2, the backsheet 30 has a core-facing side 30a and a garment side 30b. At least a portion of the core-facing side 30a of the backsheet 30 will ordinarily face the core 36. It is also within the scope of the present invention for portions of the core-facing side 30a of the backsheet 30 (such as wings 62) to be folded so that they may not necessarily always face the core 36. However, the core-facing side 30a of the backsheet 30 can be distinguished from the garment side 30b of the backsheet 30 because the core-facing side 30a is the side of the backsheet 30 that is joined to the topsheet 28 and core 36. The garment side 30b of the backsheet 30 generally forms the garment surface 20b of the sanitary napkin 20. FIG. 1 shows that the backsheet 30 has two longitudinal edges 30c and two end edges 30d.

The backsheet 30 may be any flexible, liquid impervious material that prevents discharges collected by the sanitary napkin 20, (particularly discharges which may not be completely absorbed by the core 36), from escaping the sanitary napkin 20 and soiling the undergarments and clothing of the wearer. Preferably, the backsheet 30 is not noisy, to provide discretion for the wearer. The backsheet 30 may also be impervious to malodorous gases generated by bodily discharges, so that the malodors do not escape and become noticed by the wearer and others.

As shown in FIG. 2, the backsheet 30 is preferably comprised of two layers. In the embodiment shown in FIG. 2, the backsheet 30 may comprise a first layer 32 of lofted material disposed on the core-facing side 30a of the backsheet 30. The purpose of the first layer 32 is to provide a comfortable, non-irritating surface against the body of the wearer. The lofted layer may be comprised of any suitable material, such as a nonwoven material. Preferably, the lofted layer comprises a hydrophobic nonwoven material. The second layer 34 may be disposed on the garment side 30b of the backsheet 30, and may comprise a fluid impervious film. A low density polyethylene material about 0.01 to about 0.05 millimeters in thickness, preferably about 0.02 millimeters in thickness, has been found to work well as this second layer 34. A polyethylene film, such as is sold by the Ethyl Corporation, Visqueen Division, under model XP-39385 has been found particularly well suited for this second layer. The backsheet 30 may also be made of a soft, cloth-like material which is hydrophobic relative to the topsheet 28. A polyester or polyolefinic fiber backsheet 30 has been found to work well. A particularly preferred soft, cloth-like backsheet 30 material is a laminate of a polyester nonwoven material and a film such as described in U.S. Pat. No. 4,476,180 issued to Wnuk on Oct. 9, 1984, which is hereby incorporated by reference herein.

FIG. 2 shows the attachment of the backsheet 30 and topsheet 28. The topsheet 28 is joined to the core-facing side 30a of the backsheet 30 along the longitudinal edges 28c of the topsheet 28. The topsheet 28 and backsheet 30 are also joined along at least one transverse line, which preferably coincides with the end edge 24a oriented toward the front of the wearer when the sanitary napkin 20 is worn. The topsheet 28 and backsheet 30 are, preferably, unattached to each other at the end edge 24b oriented toward the rear of the wearer.

The characteristics of the absorbent core 36 are also shown in FIG. 2. The absorbent core (or simply "the core") 36 serves as a means of absorbing bodily fluids. In particular, the absorbent core 36 is the means for collecting and containing bodily discharges, particularly menses, deposited thereon or which otherwise traverse through the liquid permeable topsheet 28. The absorbent core 36 has a body-facing side (or "first major surface") 36a and a garment-facing side (or "second major surface") 36b. FIG. 1 shows that the absorbent core 36 has two longitudinal edges 36c and two end edges 36d.

The core 36 need not have a total absorbent capacity much greater than the total amount of bodily discharges to be absorbed. In the embodiment shown in FIG. 2, the core 36 is preferably narrow and thin, so it is comfortable to the wearer. For the embodiment described herein the capacity of the core 36 should be at least about 2 grams of 0.9 percent saline solution. Suitable saline solution is sold by Travenol Laboratories of Deerfield, Ill.

As previously mentioned, the sanitary napkin 20 of the present invention has a liquid capacity great enough to absorb medium to high menstrual flows. Two capacities, which, depending on the size of the sanitary napkin may be the same, are determinable: test capacity and total capacity. Preferably, the napkin 20 of the present invention has a test capacity of at least about 8.0 grams, more preferably of at least about 15.0 grams, and most preferably of at least about 18.0 grams. Preferably, the napkin 20 of the present invention has a total capacity of at least about 20.0 grams, more preferably of at least about 30.0 grams, and most preferably of at least about 40.0 grams.

The test and total capacities of a sanitary napkin are determined as follows. Any panty adhesive release paper is removed from the napkin to be tested. To determine test capacity, a 4.75×14.0 centimeters portion, or any other configuration having 66.5 square centimeters, of the sanitary napkin is cut from the portion of the sanitary napkin which would be centered under the vaginal orifice when the sanitary napkin is worn. Total capacity is determined using the entire napkin minus any release paper. The article is weighed to the nearest 0.1 gram. The article is then submerged in a beaker of sterile saline, such that the article is totally submerged and is not bent or otherwise twisted or folded. The article is submerged for 10 minutes. The article is removed from the saline and suspended for two minutes in a vertical position to allow the saline to drain out to the article. The article is then placed body facing surface down onto an absorbent blotter, such as the filter paper #631 available from the Filtration Science Corp., Eaton-Dikeman Division of Mount Holly Springs, Pa. A uniform 17.6 grams per square centimeter load is placed over the article to squeeze excess fluid out. The absorbent blotter is replaced every 30 seconds until the amount of fluid transferred to the absorbent blotter is less than 0.5 grams in a 30 second period. Next, the article is weighed to the nearest 0.1 gram and the dry weight of the article is subtracted. The difference in grams is the test or total capacity of the article, whichever the case may be.

The core 36 should also be conformable and nonirritating to the skin. The core 36 should be sized to register with the topsheet 28 and backsheet 30. The core 36 is preferably positioned between the topsheet 28 and backsheet 30. The position of the core 36 prevents the absorbent material of the core 36 from shredding or becoming detached while the sanitary napkin 20 is worn. The position of the core 36 also ensures proper containment of bodily discharges. The core 36 may be of any suitable shape. Preferably, the core 36 is either rectangular or hourglass-shaped.

The absorbent core 36 can be made of a number of different types of materials. Suitable core 36 materials include combinations of airfelt, such as cellulose wadding and fibrated communition pulp; layers of tissue paper; and absorbent gelling materials. A suitable tissue paper core can be made in accordance with U.S. Pat. No. 4,191,609 issued Mar. 4, 1980 to Trokhan, which is hereby incorporated by reference herein. If absorbent gelling materials are used in the core 36, particularly preferred absorbent gelling materials are those made in accordance with U.S. Pat. No. 4,654,039 issued Mar. 31, 1987 to Brandt, et al. which is hereby also incorporated by reference herein.

Preferably, the core 36 comprises a laminate of absorbent gelling materials and tissue. A suitable laminate of absorbent gelling materials and tissue may be purchased from the Grain Processing Corporation of Muscatine, Iowa, under Model Number L535. A particularly preferred and illustrated core 36 has two layers of tissue with absorbent gelling materials 42 disposed between the layers. The two layers can be formed from a single sheet of tissue that is folded over on itself as shown in FIG. 2. Alternatively, the two layers can be provided by separate sheets of tissue. In the latter case, the two layers can either be made of the same material, or of different materials. For example, the upper half of the core, that is, the layer 38 that is closer to the topsheet 28, can be made of a wet laid tissue having a wet tensile strength of about 15 grams per centimeter of width. The lower half of the core, that is, the layer 40 closer to the backsheet 30, can be made of an air laid tissue containing about 0.005 grams per square centimeter absorbent gelling materials. This dual layered core 36 arrangement provides the advantage that the tissue layers prevent contact of the absorbent gelling material with the body of the wearer.

3. The Spacing Structure for Separating the First Set of Components

The first set of components capable of separation comprises the topsheet 28 and the absorbent core 36.

The liquid pervious spacing structure 44 for moving (or "spacing") the topsheet away from the absorbent core is shown in FIG. 2. The liquid pervious spacing structure 44 may also be referred to herein by any abbreviated version of its name, including, but not limited to "the spacing structure" (Alternatively, the spacing structure 44 may be referred to by a name that describes its characteristics, such as the "compressible structure" or the "deformable structure"). As its name suggests, the spacing structure 44 facilitates the separation of the first set of components.

The purpose of the spacing structure 44 is to provide the sanitary napkin 20, particularly the topsheet 28, with improved contact with the wearer's body. The spacing structure 44 advantageously utilizes the compressive forces exerted by the upper portions of the wearer's thighs. (The "upper portions" of the wearer's thighs include, but are not limited to those portions of the thighs that are in direct contact with the sanitary napkin 20 when the sanitary napkin is worn.) While not wishing to be bound by any particular theory, it is believed that when the sanitary napkin 20 is subjected to the compressive forces of the thighs of the wearer, the shape of the spacing structure 44 will be deformed so that at least a portion of the upper portion 46 of the spacing structure 44 assumes a convex upward configuration. A "convex upward" configuration is one that is vaulted or arched so that the top of the arch is upward (i.e., adjacent the topsheet 28), and the bases of the arch are adjacent the core 36. The compressive forces cause parts of the spacing structure 44, along with at least a portion of the topsheet 28 that is disposed above the spacing structure 44, to move apart from the absorbent core 36 toward the wearer's vaginal introitus.

As shown in FIG. 2, the spacing structure 44 is positioned between the topsheet 28 and the absorbent core 36. The spacing structure 44 can also be positioned in other places. For instance, as shown in FIG. 6, the spacing structure 44 could be positioned between the optional wicking layer 58 and the core 36. In such an embodiment, wicking layer 58 can be provided with absorptive capacity and can serve an absorptive function. When this is the case, the wicking layer 58 may be considered to be a part of the absorbent core 36. Therefore, in the embodiment shown in FIG. 6, the spacing structure 44 may be considered to be positioned within the absorbent core 36, or possibly even a part of the core 36.

The spacing structure 44 (and the sanitary napkin 20 in general) has an uncompressed configuration and a compressed configuration. The sanitary napkin 20 and the spacing structure 44 are shown in an uncompressed configuration in FIG. 2, and in a compressed configuration in FIG. 4. As used herein, the term "uncompressed" refers to the conditions that the sanitary napkin 20 and the spacing structure 44 are under before any compressive forces, particularly any laterally compressive forces are applied to the sanitary napkin 20. The term "compressed" refers to the conditions that the sanitary napkin 20 and the spacing structure 44 are under when such laterally compressive forces are applied. The term "laterally compressive forces" refers to forces applied (from the longitudinal edges 22) inward in the transverse direction toward the center of the sanitary napkin 20 (shown by arrows F in FIG. 4). Since the mere act of putting the sanitary napkin 20 on will likely subject it to some laterally compressive forces, the sanitary napkin 20 may only be in an uncompressed configuration before it is put on by the wearer.

The overall characteristics of the spacing structure 44 are shown in FIGS. 1 and 2. As shown in FIG. 1, the spacing structure 44 has its own longitudinal centerline $l_2$ and transverse centerline $t_2$. The longitudinal and transverse centerlines of the spacing structure 44 are useful to describe, among other things, the position and orientation of the spacing structure 44 under the surface of the topsheet 28. The spacing structure 44 may be positioned in various locations under the surface of the topsheet 28. For instance, the spacing structure 44 may be centered relative to the other components of the sanitary napkin 20 so that the longitudinal and transverse centerlines of the spacing structure $l_2$ and $t_2$, coincide with the principal longitudinal and transverse centerlines $l_1$ and $l_2$ of the sanitary napkin 20. Alternatively, the spacing structure 44 may positioned so that it is not centered on the sanitary napkin 20 and the centerlines of the spacing structure 44 are offset from either of the principal centerlines of the sanitary napkin 20. In the embodiment shown in FIG. 1, the spacing structure 44 is centered relative to the centerlines of the sanitary napkin 20.

The spacing structure 44 can also be either symmetrical or asymmetrical about the principal longitudinal and transverse centerlines, $l_1$ and $t_1$, and about its own longitudinal and transverse centerlines $l_2$ and $t_2$. In the embodiment shown in FIGS. 1 and 2, the spacing structure 44 is symmetrical about both its own longitudinal and transverse centerlines $l_2$ and $t_2$ and about the principal longitudinal and transverse centerlines $l_1$ and $t_1$.

The spacing structure 44 can be an element of any shape provided it is capable of spacing the topsheet 28 away from the core 36 when it is subjected to the laterally compressive forces described above. The overall spacing structure 44 should, therefore, be laterally compressible. As used herein, the term "laterally compressible" means that portions of the spacing structure 44 will move inward (rather than tend to spring back) when the spacing structure 44 is subjected to laterally compressive forces. The spacing structure 44 should also be deformable in the sense that when the sides 52 of the spacing structure 44 are moved inward, at least part of the top of the spacing structure 44 will "pop up". The spacing structure 44 may be compressible because it is comprised of one or more pieces of a material that is inherently compressible. Preferably, however, the material comprising the spacing structure 44 is ordinarily not inherently compressible, but is arranged into a form or configuration, by folding or otherwise, that renders it laterally compressible.

In one preferred embodiment shown in FIG. 2, the spacing structure 44 is in the form of a folded sheet of material. The sheet of material has two sides. In the embodiment shown in FIG. 2, one side, body-facing side 44a, faces the body of the wearer when the sanitary napkin 20 is worn and the other side, garment-facing side 44b, faces the wearer's undergarments. The sheet of material has a longitudinal dimension and a transverse dimension. Generally, the longitudinal dimension of the sheet will be greater than the transverse dimension, but the opposite relationship is possible. The sheet typically has two longitudinal edges, designated 44c, that generally run in the longitudinal direction when the sheet is placed in the sanitary napkin 20. The portions of the sheet located adjacent the longitudinal edges are the "longitudinal edge portions" 44c'. The sheet of material will also usually have two transverse edges or ends 44d (which in the embodiment shown in FIGS. 1 and 2, also form the transverse edges or ends of the spacing structure 44).

The sheet of material is generally folded about at least one (imaginary) axis that runs in the longitudinal direction. The sheet of material may have identifiable fold lines or creases, but such fold lines are not essential. If the sheet is arranged in the form of a tube, for instance, it will not have any identifiable fold lines. If the sheet of material has identifiable fold lines, they will also generally be oriented in the longitudinal direction. The sheet can be folded about any number of axes, from one to a virtually infinite number. In the preferred embodiment shown in FIG. 2, the sheet is folded in two places. The folds 44e are located in the longitudinal edge portions 44c' of the sheet near the longitudinal edges 44f of the spacing structure 44. The folds 44e give the folded sheet a "spring-like" property.

Figure 7:
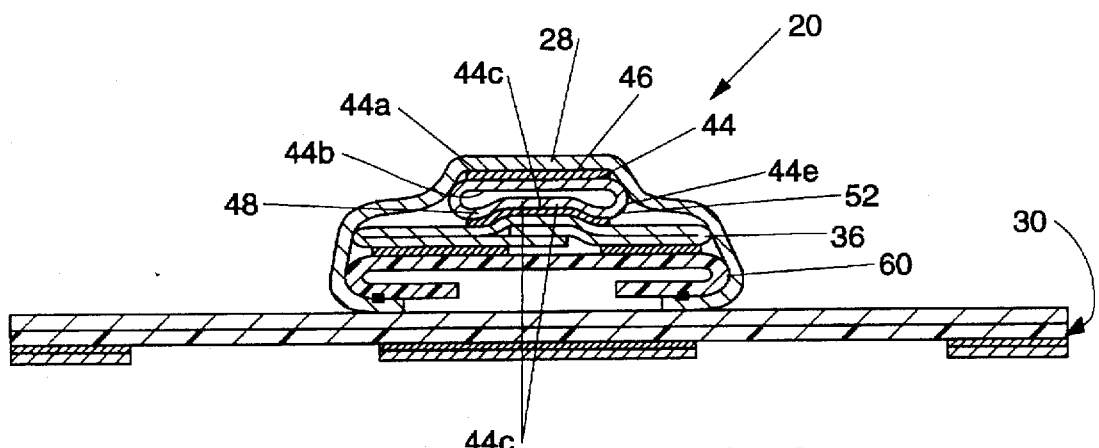
Figure 8:
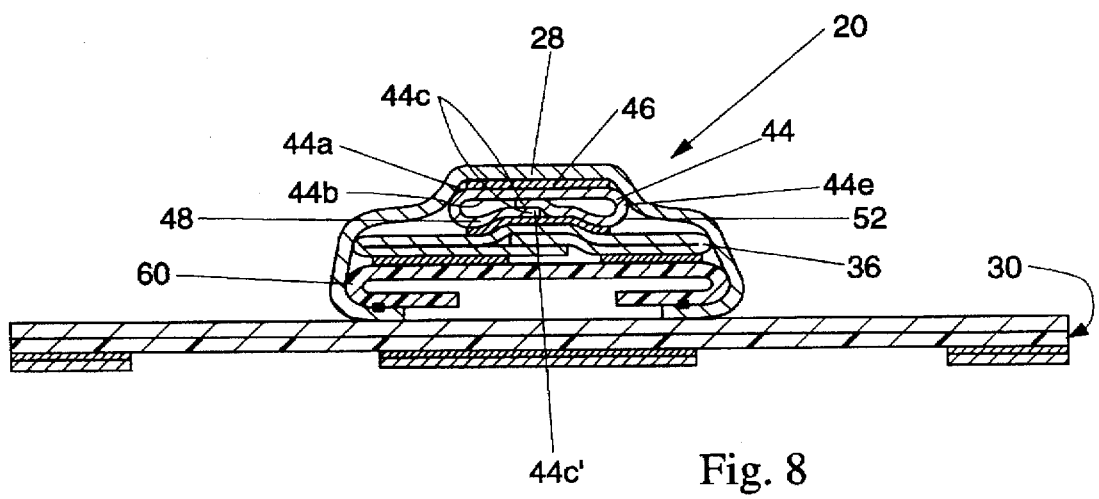

The sheet of material can be folded in many different ways. Suitable folded configurations include configurations in which the longitudinal edge portions 44c' of the sheet are folded to either overlie or be disposed under one side of the sheet. Other suitable configurations include configurations in which the longitudinal edge portions 44c' of the sheet are folded to overlie opposite sides of the sheet, such as when the sheet is folded into a z-folded configuration. In the embodiment shown in FIG. 2, the longitudinal edge portions 44c' are folded under one side of the sheet, the garment-facing side 44b of the sheet. The sheet is folded so the folds 44e are located along the longitudinal edges of the folded sheet of material (which, in this case are the same as the longitudinal edges 44f of the spacing structure 44). In other words, the folds 44e are on the lateral sides 52 of the spacing structure 44. The sheet may be folded so that the longitudinal edges 44c are spaced apart (shown in FIGS. 2 and 4), meet (FIG. 7), or overlap (FIG. 8).

Figure 9:
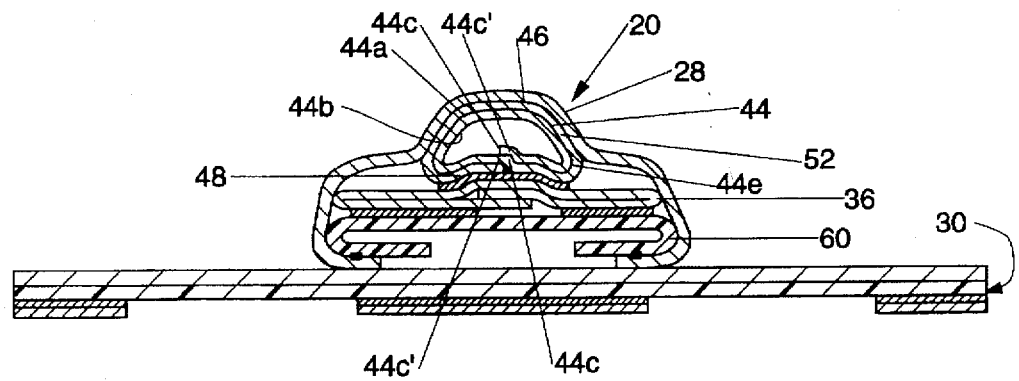
Figure 10:
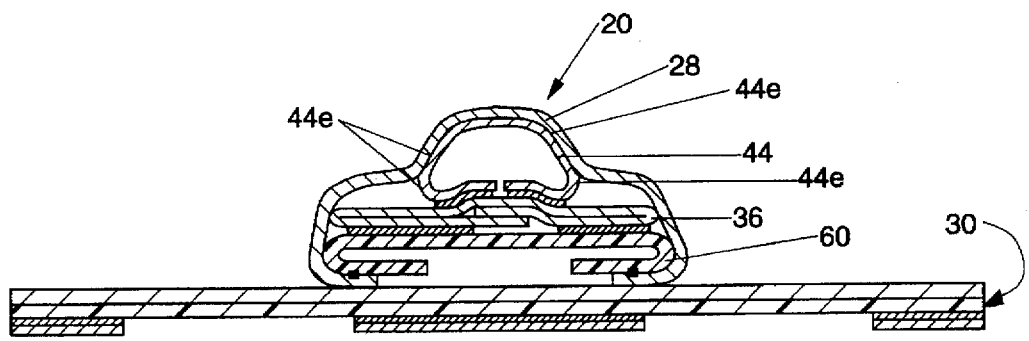
Figure 12:
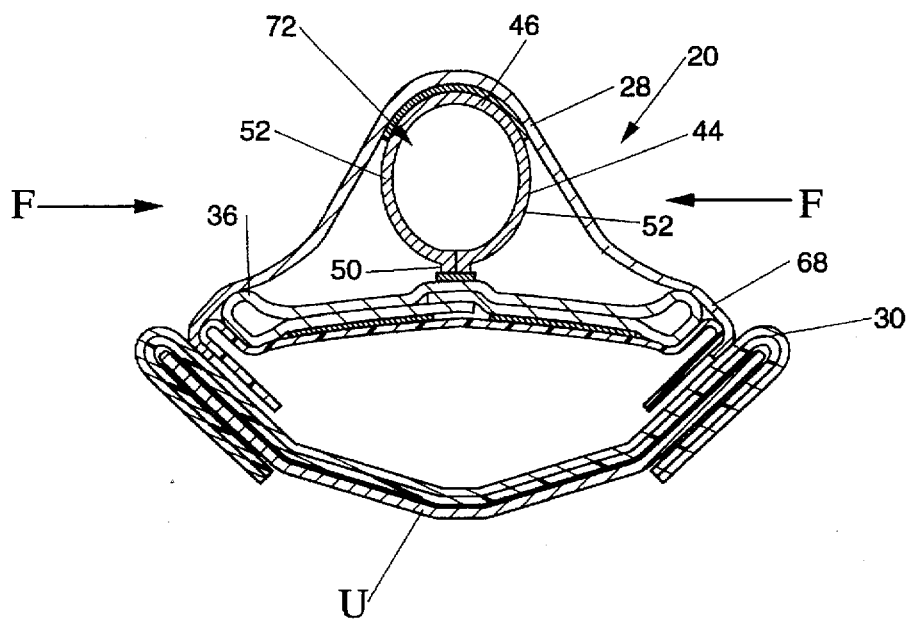
FIGS. 12 and 13 show different types of supports for the spacing structure.

The spacing structure 44 could be in the form of a tube (as shown in FIG. 12), or (as in FIG. 9) in the form a roll of more than one revolution. In addition, such a tube or roll can be flattened (as shown in FIGS. 7 and 9, respectively). As used herein, the term "flattened" means compressed in the Z-direction. The transverse cross-sectional shape of different embodiments of the spacing structure 44 can vary. For instance, the cross-section can be flattened so it appears as two layers, or it can be round, oval, elliptical, polygonally-shaped (FIG. 10), or C-shaped prior to its deformation. The shape of spacing structure 44 should be such that it does not have any sharp corners, edges, or fold lines (at least on its upper portion 46) that would irritate the wearer. Preferably, as shown in FIG. 2, the spacing structure 44 is a C-shaped (or C-folded) piece of material. In the embodiment shown in FIG. 2, the piece of material is oriented so that the opening of the letter "C" formed by the folding is facing the absorbent core 36.

Figure 7A:
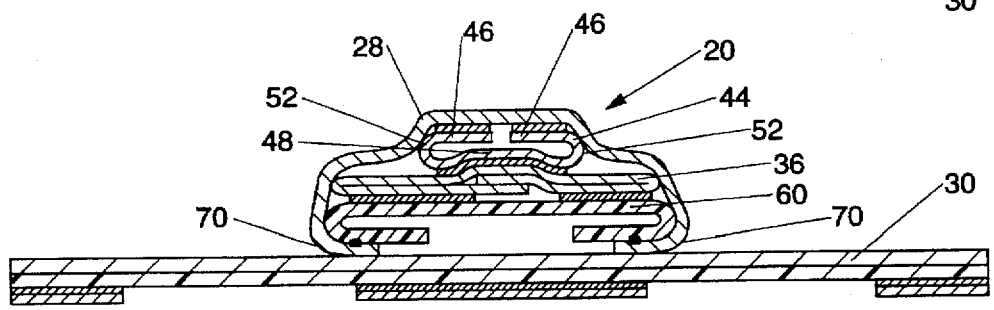
FIGS. 7A–11 show alternative versions of the spacing structure.

A variation of the C-folded spacing structure 44 is shown in FIG. 7A. In the embodiment shown in FIG. 7A, the C-folded material is oriented so that the opening of the C-fold is facing the topsheet 28. For the spacing structure 44 shown in FIG. 7A to work properly, the upper portion 46 of the spacing structure 44 should be secured to the component (such as topsheet 28) that is positioned immediately above.

Figure 11:
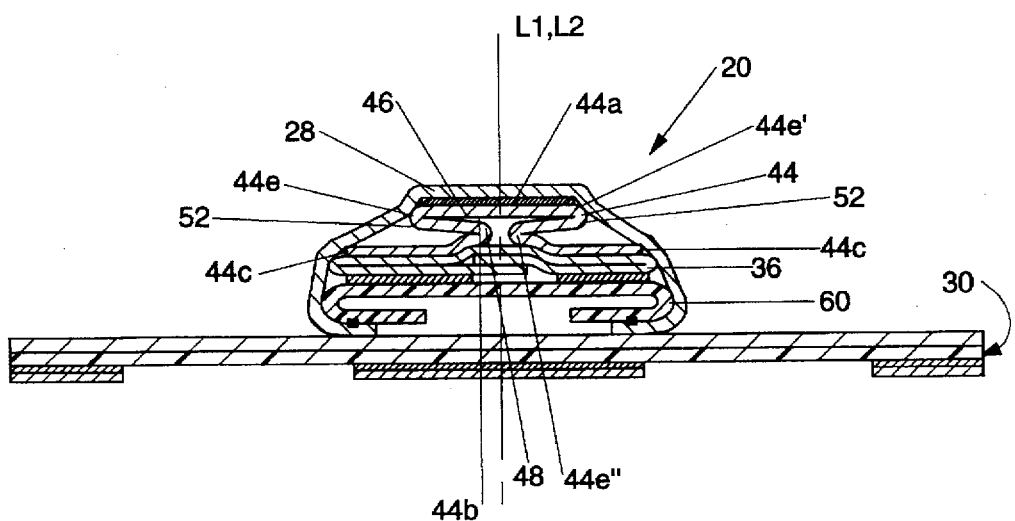

The spacing structure 44 could alternatively be in any other suitable folded configuration, including the modified C-folded configuration shown in FIG. 11. The spacing structure 44 shown in FIG. 11 is a sheet of material with two sets of longitudinal folds 44e' and 44e', one of which is disposed above the other, and longitudinal edges 44c which extend outward from the longitudinal centerline $l_2$ toward the (longitudinal) edges 36c of the absorbent core 36. The first pair of longitudinal folds 44e' comprises one fold on each side of the longitudinal centerline $l_2$ of the spacing structure 44. The first pair of folds 44e' occur where the sheet has been folded inward under the garment-facing side 44b of the sheet. The second pair of folds 44e' comprises two opposed folds where the sheet has been folded in opposite directions outward under the garment-facing side 44b of the sheet. In the embodiment shown in FIG. 11, one fold of the second pair of folds 44e" is on each side of the longitudinal centerline $l_2$ of the spacing structure 44. In other embodiments, these folds can be closer together so they meet at the longitudinal centerline $l_2$. As shown in FIG. 11, the second pair of folds 44e" are positioned inboard (i.e., closer to the longitudinal centerline $l_2$) than the first pair of folds 44e'. In the embodiment shown in FIG. 11, the longitudinal edges 44c of the folded sheet extend outward away from the principal longitudinal centerline $l_1$ approximately the same distance as the longitudinal edges 36c of the absorbent core 36. In other embodiments, the longitudinal edges 44c may only extend part of the distance to the longitudinal edges 36c of the core 36.

As shown in FIG. 1, the spacing structure 44 has a longitudinal dimension and a transverse dimension. (As shown in FIG. 2, these dimensions of the spacing structure 44 will generally be different from the longitudinal and transverse dimensions of the sheet before it is folded.) The longitudinal dimension of the spacing structure 44 should be greater than the transverse dimension so that the spacing structure 44 will be able to conform a portion of the body surface 20a of the sanitary napkin 20 to the space between the wearer's labial tissue. The spacing structure 44 can extend from between about 5% to about 100% of the length of the absorbent core 36. The absolute length of the spacing structure 44 may, thus, be between about 0.75 inches (about 2 cm.) and about 12.5 inches (about 32 cm.), preferably, about 14 cm. Preferably, the spacing structure 44 will extend approximately 70% of the length of the absorbent core 36. The width of the spacing structure 44 should extend between about 20% to about 80% of the width of the core 36, preferably between about 30% to about 70%, so the spacing structure 44 will be compressed when the sanitary napkin 20 is subjected to lateral compressive forces, yet will still be narrow enough so that it can conform to the wearer's anatomy. The absolute width of the spacing structure 44 may, thus, be between about 2 cm. and about 6 cm. Preferably, the width of the spacing structure 44 is about 1.5 inches (about 4 The plan view shape of the spacing structure 44 (that is, the shape of the spacing structure 44 when viewed from directly above) when the sanitary napkin 20 is in its flat, laid out condition of FIG. 1, can also vary. For instance, the plan view shape of the spacing structure 44 can be rectangular, oval, or some other suitable shape. In the embodiment shown in FIG. 1, the plan view shape of the spacing structure 44 is rectangular.

The spacing structure 44 comprises an upper portion 46, a lower portion 48, and opposed lateral sides (or "sides") 52. It should be understood that the designation of certain portions of the spacing structure 44 as an upper portion, a lower portion, and lateral sides is primarily for convenience of description, rather than to specify that one portion of the spacing structure 44 is necessarily a separate element or is comprised of a separate piece of material. The division of the spacing structure 44 into portions is used to describe the overall configuration of the spacing structure 44. The division of the spacing structure 44 into portions is also used to describe the shape of the spacing structure 44 before and after it has been subjected to laterally compressive forces. The different portions of the spacing structure 44 are also useful in describing the general way the spacing structure 44 moves in response to compressive forces.

The portions of the spacing structure 44 may all be comprised of the same piece of material (i.e., the spacing structure 44 may be unitary). Alternatively, the portions of the spacing structure 44 may be comprised of one or more separate pieces of material. Preferably, as shown in the preferred embodiment of the present invention of FIG. 2, the spacing structure 44 is unitary. In addition, as shown in FIG. 2, the beginning and end of some portions of the spacing structure 44 may often not be marked by a precise line of demarcation. This is particularly true in the case of the opposed lateral sides 52 of the spacing structure 44. As shown in FIG. 2, for instance, it may not necessarily be easy to tell where the lateral sides 52 of the spacing structure 44 end and the upper portion 46 begins. The lack of precise boundries between the different portions of the spacing structure 44 is not critical, however, since the division of the spacing structure 44 into portions is primarily for convenience of description. The different portions of the spacing structure 44 are sufficiently defined below so that one should be able to tell whether a given spacing structure has an upper portion, a lower portion, and opposed lateral sides.

The upper portion 46 of the spacing structure 44 is shown in FIG. 2. The "upper portion" overlies other parts of the spacing structure when the spacing structure 44 is in its uncompressed configuration. As used herein, the term "overlies" refers to the relationship in which a portion of the sanitary napkin 20 is disposed over another portion in the Z-direction when the sanitary napkin 20 is in its flat, laid out configuration of FIG. 1. A sanitary napkin will be considered to have a spacing structure with an "upper portion" within the meaning of that term as used herein, if any parts of the spacing structure in issue overlay other parts of the spacing structure.

The upper portion 46 is positioned between the topsheet 28 and the lower portion 48. In the embodiment shown in FIG. 2, when there is no other layer positioned between the upper portion 46 and the topsheet 28, the upper portion 46 is adjacent at least a portion of the (core-facing side 28b of the) topsheet 28.

At least some of the upper portion 46 contacts the component that lies immediately above it to form a contact area 54. The term "contact area" refers to the area on the surface of the spacing structure 44 that is in contact with the component above. The upper portion 46 need only be in contact with the component that lies above it at some stage when the spacing structure 44 is being compressed (when the spacing structure 44 moves from an uncompressed configuration to a compressed configuration). The forces exerted on the contact area 54 cause the topsheet 28 to move apart from the absorbent core 36. In the embodiment shown in FIG. 2, the component immediately above the spacing structure 44 is the topsheet 28. Alternatively, the component positioned above the upper portion 46 could be a pervious or absorbent component of some type that is positioned between the upper portion 46 and the topsheet 28. For ease of description, the upper portion 46 will usually be described throughout this discussion as being in contact the topsheet 28. It should be understood, however, that the description will apply equally well to the situation in which the upper portion 46 is in contact with such an other component.

The upper portion 46 of the spacing structure 44 can be secured to the topsheet 28. More specifically, the upper portion 46 may be secured to the core-facing side 28b of the topsheet 28. In alternative embodiments, however, the spacing structure 44 may be unsecured to the topsheet 28. In the embodiment shown in FIG. 2, the spacing structure 44 is secured to the topsheet 28 by topsheet securement means 74. In FIG. 2, the topsheet securement means 74 is an adhesive.

The topsheet securement means 74 can extend over any portion of the total surface area of the topsheet 28 between the longitudinal and transverse edges, 28c and 28d, of the topsheet 28. The topsheet securement means 74 may, thus, as shown in FIGS. 2 and 3, coincide in area with all of the surface area of the upper portion 46. Alternatively, the topsheet securement means 74 may coincide with only part of the surface area of the upper portion 46.

The topsheet securement means 74 may also extend outwardly beyond the transverse and longitudinal edges 44d and 44f of the spacing structure 44. Any portions of the topsheet securement means 74 that extend beyond the edges of the spacing structure 44 will serve to secure the core-facing side 28b of the topsheet 28 to the absorbent core 36. Preferably, the topsheet securement means 74 is adjacent or inboard of at least the ends 44d of the spacing structure 44. The topsheet securement means 74 could, however, be inboard of one end 44d and outboard of the other. Preferably, the topsheet securement means 74 is at least inboard of the end 44d' of the spacing structure 44 located to the rear of the wearer when the sanitary napkin 20 is worn.

The topsheet securement means 74 should not inhibit flow of menses and other exudates to the core 36. If the topsheet securement means 74 is an adhesive, the path of flow to the core 36 can be preserved in several ways, including by spreading the adhesive sufficiently thin so that a plurality of the apertures in the topsheet material are not covered with adhesive. Alternatively, the adhesive could be soluble so that is dissolves when contacted by bodily fluids. Many types of adhesives are suitable for use as the topsheet securement means 74, including water-based adhesives and hot melt adhesives.

As shown in FIG. 2, (at least a portion of) the lower portion 48 of the spacing structure 44 is adjacent the core 36 of the sanitary napkin 20 when the spacing structure 44 is in its uncompressed configuration. The lower portion 48 lies under other parts of the spacing structure 44 when the spacing structure 44 is in its uncompressed configuration. As used herein, the term "under" refers to the relationship in which a portion of the sanitary napkin 20 is disposed below another portion in the Z-direction when the sanitary napkin 20 is in its flat, laid out configuration of FIG. 1. A sanitary napkin will be considered to have a spacing structure with a "lower portion" within the meaning of that term as used herein, if any parts of the spacing structure are positioned below other parts of the spacing structure.

In the embodiment shown in FIG. 2, part of the spacing structure 44 forms at least one support 50 for the rest of the spacing structure 44. The term "support" is used herein to refer to the "legs" that the spacing structure 44 stands on when it rises up to its compressed configuration. The supports 50 may, thus, be thought of as being for the upper portion 46 of the spacing structure 44. The supports 50 may be comprised of all or parts of the lower portion 48. The supports 50 may, in addition, or alternatively, also be comprised of all or parts of the opposed lateral sides 52. As shown in FIG. 2, the portions of the spacing structure 44 that comprise the supports 50 depend in part on the way the spacing structure 44 is secured to the absorbent core 36. If the entire lower portion 48 of the spacing structure 44 is secured to the core, the supports 50 will be at least partially comprised of the lateral sides 52 since the lower portion 48 will not stand up.

Figure 13:
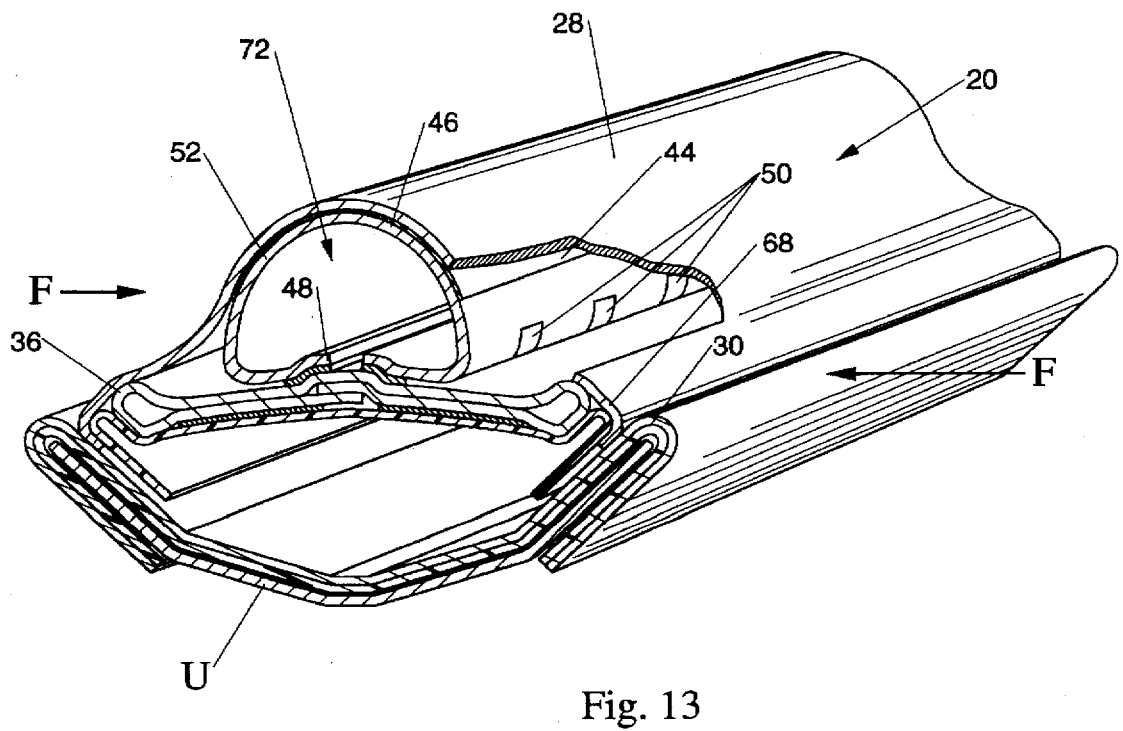

Typically, as shown in FIG. 2, there will be at least two supports 50, one on each side of the longitudinal centerline $l_2$ of the spacing structure 44. The supports 50 are preferably also on each side of the principal longitudinal centerline $l_1$ of the sanitary napkin 20. Each support 50 comprises at least parts of the longitudinal edge portions 44c' of the folded sheet. In FIG. 2, these individual supports 50 are designated 50a and 50b. FIG. 12 shows an example of a situation in which the spacing structure 44 may be considered to have only one support 50. An example of a situation in which there may be more than two supports 50 is shown in FIG. 13. Such a situation could occur when the longitudinal edge portions 44c' are comprised of discontinuous segments of material. Thus, if as shown in FIG. 13, there are five such segments on each side of the spacing structure 44, there would be a total of ten supports 50.

In several of the embodiments described herein, at least a section of the lower portion is connected to at least part of the core 36 to define an attached section 48a of the lower portion 48. Generally, at least one of the supports 50 may be connected to the core 36. Although both supports 50 are connected to the core 36 in the embodiment shown in FIG. 2, in alternative embodiments, only one support 50 could be connected to the core 36. In still other alternative embodiments (such as that shown in FIG. 11), the spacing structure 44 may be unconnected to, but in contact with the core 36. An example of an embodiment in which one support 50 is connected to the core 36 occurs if sheet comprising the spacing structure 44 is folded over on itself in an e-folded configuration. In such a case, one support may be connected to the core 36, and the other may be connected to part of the spacing structure 44, rather than to the core 36.

Figure 4:
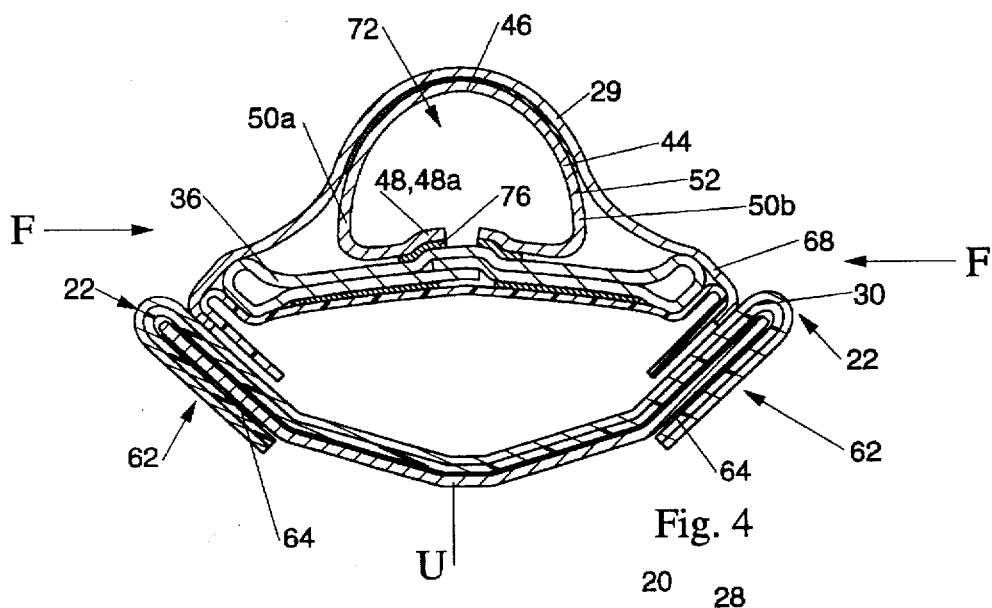
FIG. 4 is a sectional view taken from an angle similar to that of FIG. 2 which shows the sanitary napkin in a compressed configuration.

The supports 50 (or at least a portion of the supports 50) may, in some cases, be thought of as being pivotally connected to the core 36. The connection between the supports 50 and the core 36 resembles a pivot perhaps most when the material that comprises the spacing structure 44 is relatively stiff. If the supports 50 are described as being "pivotally connected" to the core 36, it is meant that there is an axis about which (at least portions of) the supports 50 may turn. Preferably, the axis is oriented in the longitudinal direction. It should be understood that it is not necessary that the supports 50 be able to rotate a full 360° around this axis, however. As shown in FIGS. 2 and 4, it is only necessary that the supports 50 rotate sufficiently to allow the spacing structure 44 to rise up from its uncompressed configuration to its compressed configuration when the sanitary napkin 20 is compressed. It is also not necessary that there be a shaft or pin about which the supports 50 turn as is sometimes thought of in the case of a pivotal connection. Typically, the function normally served by a pin will be supplied by the means (such as one or more lines of adhesive) used to secure the supports 50 to the core 36.

The supports 50 can be affixed to the core 36 in many different ways. The primary requirements of the manner of affixing the supports 50 to the core 36 is that the means used to do so be sufficient to allow the spacing structure 44 to pop up when the sanitary napkin 20 is compressed, and that the manner be stable enough so that the spacing structure 44 does not get pushed over to one side when compressive forces are applied. The means used, ("securement means" 76), will typically be an adhesive, or some other suitable means. There should be at least one region where the supports 50 are secured to the core 36. Preferably, the means used to secure the supports 50 to the core 36 is oriented in a generally longitudinal direction. Such an orientation allows the spacing structure 44 to align with the space between the wearer's labial tissue when the sanitary napkin 20 is worn. If only a single region of securement is used, it should be disposed near the longitudinal centerline $l_2$ of the spacing structure 44.

In the embodiment shown in FIG. 4, there are at least two spaced apart securement means 76 that are disposed on opposite sides of the longitudinal centerline $l_2$ of the spacing structure 44. In certain instances, the spaced apart securement means 76 may be preferred because such a construction will make it easier for the spacing structure 44 to pop up and will stabilize the spacing structure 44 by reducing the chance that it could be pushed over to one side.

In the embodiment shown in FIGS. 2 and 4 that has two spaced apart securement means 76, the configuration of the securement means 76 can vary. It is preferable, however, that such spaced apart securement means 76 are generally longitudinally oriented. They, or parts of them could be oriented at an angle to the longitudinal centerline $l_2$ so long as they are generally longitudinally oriented. In the embodiment shown, the principal longitudinal centerline $l_1$ of the sanitary napkin 20 coincides with the longitudinal centerline $l_2$ of the spacing structure 44, and the securement means 76 are parallel to and spaced equidistant from the longitudinal centerline $l_1$ of the sanitary napkin 20.

The width of each of the securement means 76 and the distances that the inside and outside edges of the securement means 76 are spaced from the principal longitudinal centerline $l_1$ can vary in different embodiments. Preferably, the widths of each individual region (e.g., line, strip, or other pattern) of adhesive that comprises the securement means 76, and the total width of the securement means 76 is less than or equal to the width of the lower portion 48 of the spacing structure 44. In one preferred embodiment where there are two spaced apart regions of adhesive, each of the regions of adhesive is approximately 0.25 inches (0.64 cm.) wide, and are on opposite sides of the principal longitudinal centerline $l_1$ and spaced approximately 6 mm. apart between their inside edges. In this embodiment the length of the securement means 76 extends the full length of the spacing structure 44.

The adhesive may be applied in any suitable spray pattern, such as spiral, or in longitudinally oriented beads. In addition, the securement means 76 could be continuous or intermittent. Preferably, however, the securement means are continuous or nearly continuous. In addition, the upper portion 46 of the spacing structure 44 is preferably unsecured to any component lying below between its longitudinal edges 44f so that the spacing structure 44 will be able to stand up when compressed.

The lateral sides 52 in the spacing structure 44 shown in FIG. 2 comprise at least the two folded edges of the folded sheet of material. An absorbent article will be considered to have a spacing structure with "opposed lateral sides" as that term is used herein, if its spacing structure has any portions which are capable of moving inward toward each other when the spacing structure is compressed from the sides. Typically, when a reference is made to "compressing" the spacing structure 44, this means that the spacing structure 44 is subjected to compressive forces that are being applied to the sanitary napkin 20 as a whole, rather than to just the spacing structure 44. In other words the spacing structure 44 is typically compressed indirectly by the forces that are transmitted through the other components of the sanitary napkin 20.

The spacing structure 44 is flexible in that when the spacing structure 44 is compressed from the sides, the sides 52 may move inwardly toward the longitudinal centerline $l_2$. This results in at least some of the contact area 54 of the upper portion 46 moving the topsheet 28 apart from the absorbent core 36 in a direction generally perpendicular to the principal longitudinal and transverse centerlines of the sanitary napkin 20 (i.e., in the Z-direction). The shape of the spacing structure 44 should render the spacing structure 44 resilient enough that it will deform into the desired shape, but will not have a tendency to return to its uncompressed configuration unless the laterally compressive forces are removed. The spacing structure 44 should preferably deform when it is subjected to the forces associated with wearing a sanitary napkin. The amount of force exerted on a sanitary napkin depends on many factors, including the size and weight of the wearer, and the activity the wearer is engaged in when the measurement is taken. It is believed that the lateral compressive forces associated with wearing sanitary napkins may be in the range of slightly over 0 (e.g., about 0.01) to about 2.5 psi., and more specifically, may be in the range of about 0.05 to about 0.5 psi. If it is necessary to determine whether the spacing structure 44 will deform under such forces, the following procedure may be used. The procedure is referred to as the Lateral Compression Test.

Lateral Compression Test

Prior to and during the Lateral Compression Test, to ensure accurate readings, the sanitary napkin 20 should not be bent, flexed, or otherwise handled in any manner that will affect the results of the test. Therefore, the sanitary napkin 20 should typically only be tested by the following procedure once.

The sanitary napkin 20 is prepared for the test by removing any optional cover strips 66 that may cover any adhesive attachment means 64 used for affixing the sanitary napkin 20 to the wearer's undergarments. This will eliminate the possibility of any excess stiffness being imparted to the sanitary napkin 20 by the cover strip 66 that would not ordinarily be present when the sanitary napkin 20 is worn. The adhesive of the attachment means 64 may be sprinkled with corn starch or baby powder to eliminate as much as possible the tackiness of the adhesive so that the adhesive will not stick to any of the testing equipment.

The sanitary napkin 20 is then placed body surface 20a up in a suitable testing device (possibly an Instron testing apparatus) that is capable of exerting lateral compressive forces inward from the longitudinal edges 22 of the sanitary napkin 20. The testing apparatus should be equipped with opposed arms that are capable of horizontal movement toward each other. Each arm should have a clamp on the end. The arms should move so that the clamps are able to exert compressive forces in a single plane, and along the same line so that the sanitary napkin 20 will not be subjected to bending or shearing forces. The clamps should be arranged so that each of the portions of the sanitary napkin 20 that are clamped will be held at an angle that is turned approximately 30° downward from horizontal.

The sanitary napkin 20 is then clamped in place in the testing device. The clamps should be affixed so that they grip the sanitary napkin 20 inward (i.e., toward the principal longitudinal centerline $l_1$) of the longitudinal edges 22 of the sanitary napkin 20 and the core 36, just outside of the longitudinal edges 44f of the spacing structure 44. The clamps should be applied so that they are in the region of the transverse centerline $t_2$ of the spacing structure 44. The appropriate compressive forces are then applied, and the decoupling of the topsheet 28 of the sanitary napkin 20 is noted, and the test is thus completed.

The spacing structure 44 used in the present invention should be sufficiently resilient that the sides 52 will not collapse inward when the structure 44 is compressed by the lateral compressive forces applied by the wearer's thighs. The degree of resiliency, however, should be such that the structure 44 will not resist deformation, but will utilize the compressive forces to deform and improve contact of the sanitary napkin 20 with the wearer's body. The spacing structure 44 itself can thus be of a configuration, due to folding or otherwise, that renders it resilient. Alternatively, or additionally, the spacing structure 44 could be comprised of a material that has some degree of inherent resiliency. Preferably, the latter is the case. Most preferably, the material which comprises the spacing structure 44 is not only resilient, but is also wet resilient so the spacing structure 44 will not collapse when the sanitary napkin 20 is wetted by exudates.

The spacing structure 44 can be made of any suitable material. The material used for the spacing structure 44 will normally be a thin sheet of flexible, liquid pervious material. Alternatively, the spacing structure 44 can be comprised of a composite of two or more layers of flexible, liquid pervious material. The material used to construct the spacing structure 44 must be such that when it is folded, it will behave in the manner specified above. The material used to construct the spacing structure 44 should also be soft and non-irritating to the wearer when the spacing structure 44 deforms under the topsheet 28. Suitable materials for use in the spacing structure 44 include nonwoven fabrics, such as tissues. A suitable tissue can be made in accordance with the patent issued to Trokhan, previously incorporated by reference. (Tissues will generally not by themselves, however, provide the spacing structure 44 with the aforementioned wet resilient properties.) Plastic nets comprising water insoluble fiber forming polymers are also suitable. Suitable polymers for such nets include polyolefines, such as polypropylene, propylene-ethylene copolymers and high density polyethelene, polyamides and polyesters.

Preferably, the spacing structure 44 is also absorbent. It is especially desirable for the spacing structure 44 to be absorbent if the topsheet 28 is made of an apertured film which is coated with a surfactant (in accordance with one suitable topsheet described above). If such a material is used for the topsheet 28, the component positioned under the topsheet 28 (e.g., the spacing structure 44) must be both absorbent and in contact with the topsheet 28 to establish the capillary gradient required to cause liquids to flow through the topsheet 28 toward the absorbent core 36. A particularly preferred absorbent material for use as the spacing structure 44 is the spunlaced nonwoven fiber sheet known as "SONTARA" that is described in Column 8 of the Osborn patent previously incorporated by reference herein.

The shape into which the spacing structure 44 deforms can vary, but this shape should have rounded rather than sharp edges so the sanitary napkin 20 will be comfortable to wear. Preferably, the overall sanitary napkin 20 deforms into a W-shape similar to that shown in FIG. 4. As shown in FIG. 4, the spacing structure 44 forms the central portion of the W-shaped configuration. In addition, the portion of the sanitary napkin 20 that is worn to the rear of the wearer should assume a configuration that will fit at least partially into the wearer's gluteal groove (i.e., groove between the buttocks).

The distance that the spacing structure 44 may space the topsheet 28 away from the core 36 can vary. This invention is intended to include absorbent articles having a spacing structure 44 that may space the topsheet 28 various different distances away from the core 36. The distance that the spacing structure 44 may space the topsheet 28 away from the core 36 depends upon a number of factors. These include the manner in which the sanitary napkin 20 is worn, and the place at which the separation is measured. For instance, the distance the topsheet 28 is spaced away from the core 36 would generally be greater in the portion of the sanitary napkin 20 which is aligned near the rear of the wearer since the spacing structure 44 will have more space to move in the region of the wearer's gluteal groove.

Preferably, the spacing structure 44 may move the topsheet 28 apart from the core 36 a distance of up to about 6 centimeters, preferably, between about 0.5 centimeters and about 4 centimeters. More preferably, the spacing structure 44 may move the topsheet 28 apart from the core 36 a distance of between about 1 centimeter and about 3 centimeters. The present invention is intended to encompass sanitary napkins having a spacing structure which is capable of spacing the topsheet away from the core when either the sanitary napkin or the spacing structure are sufficiently laterally compressed from the sides either by hand, or by mechanical means, regardless of whether such separation actually takes place when the sanitary napkin is worn.

The amount of separation of the topsheet 28 from the core 36 may be measured by the following method, which is referred to as the Topsheet Separation Test.

Topsheet Separation Test

The sanitary napkin 20 should be handled in accordance with the procedure specified above in the Lateral Compression Test (with the exception of the step of applying corn starch or baby powder to cover the adhesive of the attachment means 64).

The sanitary napkin 20 is first cut completely through in the transverse direction so that the cut passes approximately through the transverse centerline $t_2$ of the spacing structure 44. This will leave the sanitary napkin 20 open at one end.

The garment side 30b of the backsheet 30 of either half of the sanitary napkin 20 is then attached to a rigid, flat, planar surface using the attachment means 64 that is ordinarily provided for attaching the backsheet 30 to the undergarment of the wearer. The backsheet 30 is maintained in contact with and parallel to this surface. Either at this time, or at any convenient time prior thereto, the core 36 and the backsheet 30 of the sanitary napkin 20 are glued together or otherwise affixed in some suitable manner so that the topsheet 28 and spacing structure 44 will be able to separate in the intended manner from the core 36, but the core 36 will not be able to separate from the backsheet 30.

The longitudinal centerline $l_2$ of the spacing structure 44 at the open end of the sanitary napkin 20 is then located. The portion of the spacing structure 44 located at the longitudinal centerline $l_1$ is then raised or lifted in the Z-direction, that is, in a direction generally perpendicular to the flat, planar surface. The spacing structure 44 may be lifted from the flat, planar surface by inserting one end of a thin, rigid instrument (such as a rod) between the upper portion 46 of the spacing structure 44 and the core 36. For the purpose of this test, the inserted end of the rod should be inserted into the open end approximately 1 cm. The other end of the rod is lifted away from the flat, planar surface while the inserted end of the rod is used to raise the spacing structure 44.

The end of the rod is lifted away from the flat, planar surface until the spacing structure 44 is restrained from moving further without stretching the material comprising the spacing structure 44. After the spacing structure 44 is raised in this manner, the Z-direction distance between the core-facing side 28b of the topsheet 28 and the body-facing side 3a of the core 36 is measured perpendicular to the flat, planar surface. A separate scale, oriented in the Z-direction and generally perpendicular to the flat, planar surface, may be used for this measurement. The measurement is taken at the longitudinal position coincident with the transverse centerline $t_2$ of the spacing structure 44. When the measurement is taken, the test is completed.

There are certain additional characteristics that may either be present in alternative embodiments, or in preferred embodiments of the spacing structure 44. Preferably, not only does the spacing structure 44 assume a convex upward configuration, but it also assumes a shape that conforms the topsheet 28 to the shape of the wearer's labial tissue. It is even more preferable that the spacing structure 44 provide the sanitary napkin 20 with a shape so that the topsheet 28 can work its way into the space between the wearer's labial tissue. Still even more preferably, the properties of the spacing structure 44 should be such that the spacing structure 44 will cause the topsheet 28, which serves as the body-contacting element of the sanitary napkin 20, to adjust its shape in conformity with the movement of the wearer when the wearer moves about. For example, if the wearer's activities cause her legs to be close to each other, the spacing structure 44 should be more compressed or assume a more upright shape than if her legs are apart. (That is, the spacing structure 44 should have an overall width measured in the transverse direction that is less than the height of the spacing structure 44 measured in the Z-direction.) Preferably, when the wearer's activities or movements cause her legs to move back apart, the spacing structure 44 will assume a flatter shape (that is, the overall width of the spacing structure 44 will increase and the overall height will decrease).

Figure 5:
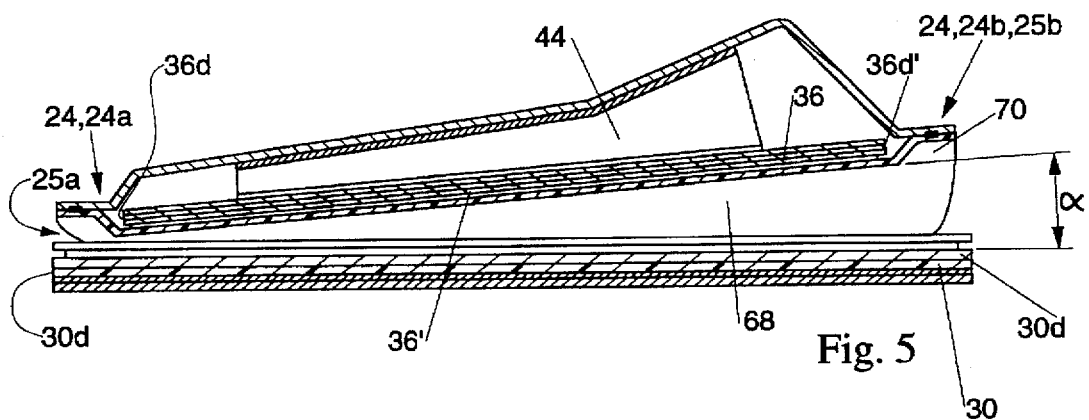
FIG. 5 is a sectional view taken from a similar angle to that of FIG. 3 which shows the sanitary napkin in a compressed configuration and articulated to the open position.

Preferably, the spacing structure 44 should also form a hollow shape when it is subjected to compressive forces. As used herein, the term "hollow" means having a cavity within. While not wishing to be bound by any particular theory, it is believed that a hollow shape will aid the spacing structure 44 in retaining its integrity when compressed. When it is said that the integrity of the spacing structure 44 is retained, it is meant that the lateral sides 52 of the spacing structure 44 will not have as great a tendency to collapse inward. As shown in FIG. 5, shape of the cavity 72 in longitudinal cross-section may be similar to that of a tube. In transverse cross-section, the cavity 72 can have many different configurations such as the irregularly-shaped configuration shown in FIG. 4. In addition to the configuration of the cavity 72 shown in FIG. 4, the configuration of the transverse cross-section of the cavity 72 could also be nearly circular, elliptical, or of different configurations in other situations and in other embodiments. As shown in FIG. 4, the spacing structure 44 defines at least a portion of the perimeter of the cavity 72. As shown in FIG. 4, when the ends of the spacing structure 44 are spaced apart, a portion of the perimeter of the cavity 72 could also be formed by part of some other element, such as a portion of the core 36. The total length of the perimeter of the cavity 72 will usually remain constant regardless of the shape of the spacing structure 44, and regardless of whether the spacing structure 44 is compressed or uncompressed.

Figure 14:
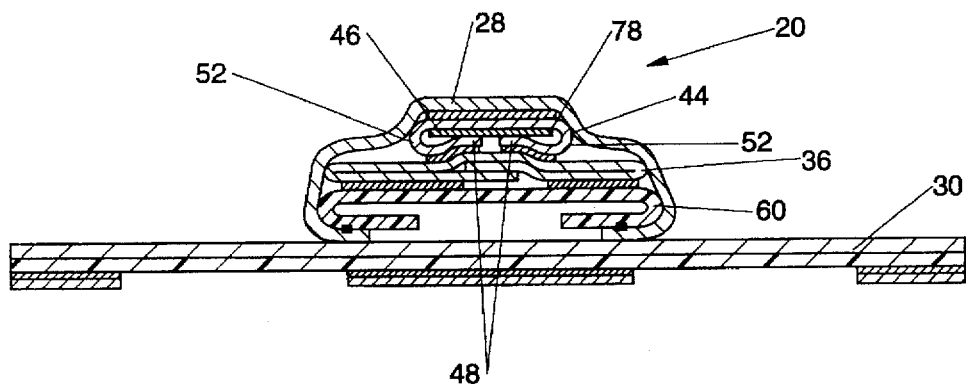
FIG. 14 is an alternative version of the sanitary napkin of the present invention that has a tissue strip positioned in the interior of the spacing structure.

In an alternative embodiment shown in FIG. 14, a tissue layer in the form of a sheet or strip 78 could be provided in the interior of the spacing structure 44 (that is, between the upper and lower portions 46 and 48).

The spacing structure 44 can also be constructed in the general form of the resilient member described in UK Patent Application 2 168 612 A (discussed above), which patent application is hereby incorporated by reference herein. However, such a resilient member must be provided with several key characteristics that are not disclosed in the UK patent application. The resilient member must be of such a construction that it allows, not resists deformation. The resilient member must be of such a configuration and must be made out of materials which makes the sides of the member move inward, instead of springing back in response to laterally compressive forces. The member must only tend to return to its original configuration when such forces are removed, if at all. In addition, the member must have an upper portion that spaces the topsheet of a sanitary napkin away from the core when the member is compressed. The member must also form a closed configuration. The longitudinal edges of the folded strip should, thus, either be bonded together, or to another component of a sanitary napkin (instead of being free and unattached as shown in the drawings of the UK patent application). The material from which the strip is fashioned must be relatively soft so that it will be comfortable for the wearer. Further, the member must be secured to the core in some manner (rather than being unsecured), so that it will not shift in position.

The spacing structure 44 can also serve functions in addition to spacing the topsheet 28 away from the absorbent core 36. For instance, the spacing structure 44 could act as a wicking layer to distribute absorbed fluids over a wider area of the absorbent core 36 to increase the absorbent capacity of the sanitary napkin 20.

4. Optional Components of the Sanitary Napkin

The sanitary napkin 20 of the present invention may be provided with optional additional components.

The sanitary napkin 20 of the present invention can be provided with one or more absorbent layers that may be positioned between the absorbent core 36 and either the topsheet 28, the backsheet 30, or both. As shown in FIG. 6, an absorbent layer, such as wicking layer 58, is positioned between the topsheet 28 and the absorbent core 36. This wicking layer 58 may be referred to as a secondary topsheet (or "wipe acquisition sheet"). In addition, in another alternative embodiment, the wicking layer 58 could have the characteristics set forth above for the spacing structure 44, and could serve as the spacing structure 44.

As illustrated in FIG. 2, a sanitary napkin 20 according to the present invention may further comprise a liquid impervious interliner 60 that is associated with the core 36 and intermediate the core 36 and backsheet 30. The interliner 60 serves as the first constraint for any bodily discharges that may tend to migrate towards the backsheet 30. However, if the interliner 60 is omitted, or if any discharges penetrate the interliner 60, such discharges should generally be intercepted and retained by the backsheet 30. The interliner 60 is generally coextensive with and preferably generally registered with the core 36.

Figure 15:
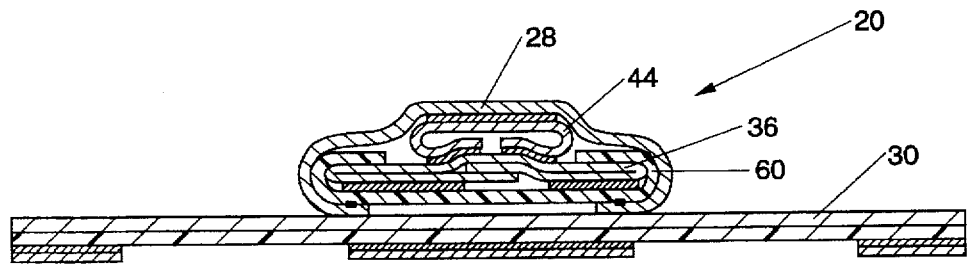
FIG. 15 shows a sanitary napkin having an optional interliner of an alternative configuration.

The interliner 60 may be joined to the core 36 across the entire surface area of the interliner 60, or any portion of the same. An arrangement in which the interliner 60 is joined to the core 36 across its entire surface area, however, results in a sanitary napkin 20 of lower flexibility. Preferably, only the periphery of the interliner 60 is joined to the core 36. In a preferred embodiment shown in FIG. 2, the interliner 60 is peripherally joined to the face 3b of the core 36 which is oriented towards the backsheet 30. Even more preferably as shown in FIG. 15, the interliner 60 wraps the longitudinal edges 36c of the core 36 and is peripherally joined to body-facing side 3a of the core 36 adjacent the longitudinal edges 36c of the core 36. The interliner 60 may be heat sealed or, preferably, adhesively joined to the absorbent core 36. A suitable material for adhesively joining the interliner 60 to the absorbent core 36 is two-sided surgical tape Number 1524 made by the Minnesota Mining and Manufacturing Company of St. Paul, Minn.

The interliner 60 is preferably relatively thin, and flexible. Preferably, the interliner 60 has a thickness less than or equal to that of the backsheet 30 so that when the sanitary napkin 20 is worn and the sanitary napkin articulates between the open and closed positions (described below), discretion in the form of quietness is provided for the wearer. An interliner 60 having a thickness of no greater than about 0.02 millimeters is suitable. If the interliner 60 is liquid impervious, it is not necessary that the backsheet 30 also be liquid impervious. In such an embodiment, the interliner 60 functions as a backsheet and the backsheet 30 need only be liquid resistant. As used herein the term "liquid resistant" refers to the property of a material which impedes the transport of liquids through and past such a material. The term liquid resistant includes liquid impervious materials. A suitable interliner 60 may be made from the low density polyethylene material, described above, used for the backsheet 30 or from X-7644 low density polyethylene film sold by the Ethyl Corporation, Visqueen Division of Terre Haute, Ind.

If desired, the sanitary napkin 20 may be additionally provided with flaps 62 that extend outwardly from each longitudinal edge 22 of the sanitary napkin 20. The flaps 62 may be made in accordance with the teachings of U.S. Pat. No. 4,589,876, issued May 20, 1986 to Van Tilburg and U.S. Pat. No. 4,687,478, issued Aug. 18, 1987 to Van Tilburg, which patents are incorporated herein by reference.

In addition, as shown in FIG. 2, the garment side 30b of the backsheet 30 may include a means for attaching the sanitary napkin 20 to the undergarment of the wearer ("attaching means") 64. Preferred attaching means 64 may include mechanical fasteners or, more preferably, adhesive fastening means, such as a pressure sensitive adhesive. The pressure sensitive adhesive may be applied to the garment side 30b of the backsheet 36 in two parallel strips or two symmetrically opposite, convex outwardly oriented strips. The strips of adhesive may be between about 5 to about 35 millimeters in width. Preferably, the strips of adhesive are sized and disposed so that in the crotch region of the sanitary napkin 20 the distance between the inside edges of the strips is about 11 mm, and the distance between the outside edges of the strips is about 60 mm. A definition of the term "crotch region" is contained in U.S. Pat. No. 4,690,680 issued to Higgins on Sep. 1, 1987, which patent is hereby incorporated by reference herein.

Alternatively, the adhesive may be applied to the backsheet 30 in a generally centered rectangular patch (not shown) covering about 30 to about 70 percent of the area of the garment side 30b of the backsheet 30. In another alternative illustrated in FIGS. 1–3, the adhesive can be longitudinally centered and disposed near the distal end of each flap 62 (i.e., the end of the flaps 62 farthest away from the principal longitudinal centerline 1 of the sanitary napkin 20). Suitable adhesive may be that specified as 0.6 mil pass available from Century Adhesive as product number A305-4, or from Anchor Continental, Inc., 3 Sigma Division, of Covington, Ohio.

5. Separation of the Second Set of Components

The second set of components that are capable of separation comprises the absorbent core 36 and the backsheet 30 of the sanitary napkin 20. The separation or decoupling of the core 36 from the backsheet 30 is first shown in FIGS. 4 and 5 of the drawings.

In viewing the drawings, particularly FIGS. 4 and 5, it should initially be understood that the drawings are merely intended to be approximate representations of the configurations that the sanitary napkin 20 may take when it is worn. Thus, the compressed configuration of the sanitary napkin 20 may be different from the specific configurations shown in the drawings. The separation of the components may also occur in manners in addition to those shown in the drawings. The scope of the present invention includes all of these other configurations and manners of separation. In addition, it should also be understood that the size of various components of the sanitary napkin 20 may be slightly exaggerated in the drawings. This has been done to better show the deformation of the spacing structure 44 and to more clearly show the separation of the components of the sanitary napkin 20.

The separation of the core 36 from the backsheet 30 may alternatively be thought of as a separation of the topsheet 28 from the backsheet 30 as described in U.S. patent application Ser. No. 07/429,252 entitled "Decoupled Sanitary Napkin", filed in the name of Osborn, et al. on Oct. 27, 1989, which is hereby incorporated by reference herein. The separation may be viewed in such a manner because if the core 36 separates from the backsheet 30, the topsheet 28 (being disposed on the other side of the core 36) will also separate from the backsheet 30. Regardless of how the separation from the backsheet 30 is thought of, it is believed that such separation is useful in providing a sanitary napkin that can be attached to the undergarment of the wearer that will also maintain a constant position with respect to the body of the wearer even though, as noted above, when the wearer moves about the wearer's undergarments may not always move in exactly the same way as the wearer's body.

In addition, by separating the topsheet 28 and core 36 from the backsheet 30, the flexibility of the portion of the sanitary napkin 20 which is adjacent to and conforms to the wearer's body is enhanced and increased. This occurs because the stiffness imparted by the backsheet 30, and any associated components, will be generally less noticeable, due to these subcomponents being decoupled and further from the body of the wearer.

The separation of the core 36 from the backsheet 30 is made possible by the manner in which the sanitary napkin 20 is constructed. Specifically, the separation occurs because of the way the core 36 is joined to the backsheet 30. The core 36 is joined to the backsheet 30 along the longitudinal edges 36c of the core 36. The core 36 may also be joined to the backsheet 30 along at least one transverse juncture 25a. The transverse juncture 25a can be a region such as a line or an edge. The core 36 is generally otherwise unattached to the backsheet 30 between its longitudinal edges 36c and at at least one end 24 of the sanitary napkin 20. The unattached portion of the core 36 is generally designated 36. The unattached portion 36' of the core 36 may move apart from the backsheet 30. Typically, the transverse juncture 25a is located in the portion of the sanitary napkin 20 that will be to the front of the wearer when the sanitary napkin 20 is worn. As illustrated in FIGS. 1–3, the transverse juncture 25a may be generally coincident with an end edge 24, such as the front end edge 24a of the sanitary napkin 20. The end edge 24 at which the transverse juncture 25a is located may be referred to as the "joined end edge" The other end edge is the "unattached end edge" 25b. Typically, the unattached end edge 25b is oriented towards the rear of the wearer when the sanitary napkin 20 is worn (i.e., it is located at end edge 24b).

The definitions of several terms are useful in understanding the joinder of the components shown in the drawings. As used herein the term "joined" refers to the condition where a first member or component is attached, or connected, to a second member or component either directly or indirectly. An "indirect" connection occurs where the first member or component is attached or connected to an intermediate member or component which in turn is attached or connected to the second member or component. The relationship between the first and second joined members or components is intended to remain for the life of the members or components. As used herein the term "unattached" refers to the condition where two members or components are not joined or otherwise intended to remain in contacting and adjacent relationship during the useful life of the disposable absorbent article. The term "affixed" refers to a temporary contacting relationship between two members or components of the sanitary napkin 20. As used herein, the term "associated" comprises integral, joined, affixed, indirectly and weakly linked relationships.

Figure 16:
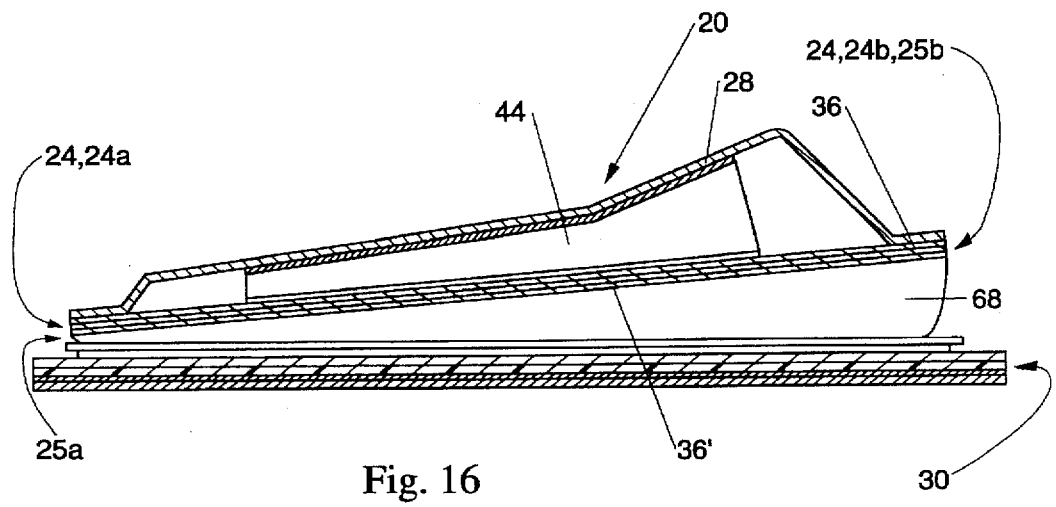
FIG. 16 is a view similar to FIG. 5 showing the sanitary napkin without the optional interliner.

As shown in FIGS. 4 and 5, the absorbent core 36 is indirectly connected to the backsheet 30. In the embodiment shown in FIGS. 4 and 5, the core 36 is connected to the optional interliner 60, and the optional interliner 60 is connected to the backsheet 30 as described above (i.e., joined at the longitudinal edges and at a transverse juncture 25a). If there is no optional interliner 60, as shown in FIG. 16, the core 36 could be directly connected to the backsheet 30 along its longitudinal edges 36c and at a transverse juncture 25a.

As noted above, the transverse juncture 25a may be referred to as an edge. The transverse juncture 25a is an edge the sense that it may be viewed as a line that is formed by the intersection of two planes, such as the plane defined by the core 36, and the plane formed by the backsheet 30. The transverse juncture 25a functions like a hinge, allowing parts of the sanitary napkin 20 (e.g., the topsheet 28, the core 36, and the interliner 60) to articulate with respect to the backsheet 30 about the joined end edge 24a. As illustrated by comparing FIGS. 3 and 5, the sanitary napkin 20 articulates between a closed position and an open position. In the "closed position" of FIG. 3, the unattached end edges, 36d' and 30d', of the core 36 and backsheet 30 are generally proximate and preferably adjacent. In the "open position" of FIG. 5, the unattached end edges, 36d' and 30d', of the core 36 and backsheet 30 are separated in the Z-direction, relative to each other, from their respective closed position locations.

As shown in FIGS. 4 and 5, the sanitary napkin 20 has a means for controlling the separation of the core 36 from the backsheet 30. The means for controlling the separation of the core 36 from the backsheet 30 prevents the sanitary napkin 20 from unintended gross deformations and from exceeding the open position. As used herein a "means for controlling the separation of the core from the backsheet" is any component which limits the relative Z-direction separation of the core 36 from the backsheet 30.

One suitable means for controlling the amount of separation of the core 36 from the backsheet 30 is by the use of a material having a longitudinally-oriented pleat (a "pleated material") 68 to join the core 36 directly or indirectly to the backsheet 30. The pleated material 68 typically, but not necessarily, has a length in the longitudinal direction generally equivalent to the longitudinal dimension of the shorter of the core 36 and the backsheet 30. The pleated material 68 also generally has at least one longitudinally oriented fold line 70, so that dual, or more than two, Z-direction layers of the material are provided along the length of the fold line 70. The pleated material 68 may be an extension of the topsheet 28, an extension of the backsheet 30, or a separate piece of material having one end joined directly or indirectly to the core 36 and the other end joined to the backsheet 30. Preferably, two pieces of material, each having longitudinally oriented pleats are provided, one near each longitudinal edge 36c of the absorbent core 36. In addition, a foreign lamina or material may also be interposed between the dual layers of the pleated material 68.

As shown in FIG. 2, a preferred longitudinally oriented pleated material 68 is provided by an extension of the topsheet 28. In the embodiment shown in FIG. 2, the topsheet 28 is in a C-folded configuration. The longitudinal ends 28e of the sheet that comprises the topsheet 28 are folded under the central portion of the topsheet 28 so they are laterally inboard of the longitudinal edges 36c of the absorbent core 36, and are joined to the backsheet 30. Joining may either be accomplished by heat sealing or adhesive bonding. The Number 1524 surgical tape sold by the Minnesota Mining and Manufacturing Company is suitable for this purpose. The longitudinally oriented pleated material 68 may have a fold line 70 between the longitudinal end 28e of the sheet that is joined to the backsheet 30 and the corresponding layer of material, which forms part of the longitudinally oriented pleat that is positioned directly above the longitudinal end 28e.

As shown in FIG. 2, the longitudinal ends 28e of the topsheet 28 are folded inwardly (i.e., towards the longitudinal centerline $l_1$) underneath the core 36 and joined to the backsheet 30. In the closed position the C-folded sheet is collapsed, and the pleats of the sheet extend transversely and have material that is flaccid in the Z-direction. When the sanitary napkin 20 is articulated to the open position, the fold lines 70 of the longitudinally oriented pleated material 68 are lifted away from the backsheet 30 in the Z-direction. This removes the slack from the flaccid material and allows separation in the Z-direction until constrained when the pleats are fully extended. Preferably, the width of the pleats (that is, the dimension measured in the transverse direction between a longitudinal ends 28e of the sheet and the fold line 70, or between the fold lines of the pleat, if there is more than one pleat) ranges from about 2 millimeters to about 15 millimeters, and is preferably about 5 millimeters to about 8 millimeters.

Figure 17:
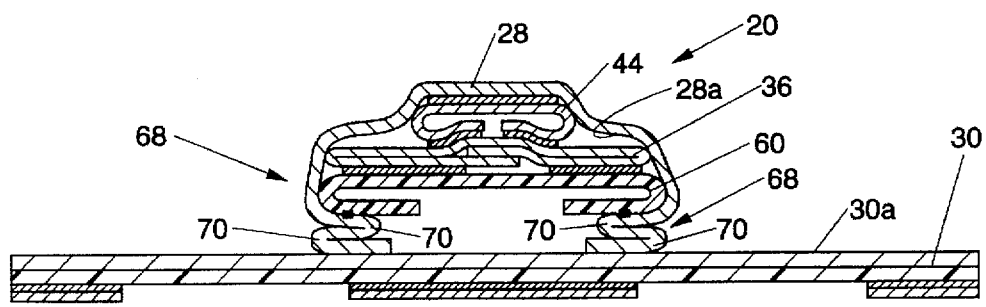
FIGS. 17–20 show alternative means for controlling the separation of the core of the sanitary napkin from the backsheet.

Another suitable means for controlling the separation of the core 36 from the backsheet 30 is by use of a material having accordion style longitudinally oriented pleats 68 as shown in FIG. 17. Such an accordian style pleated material 68 has two distal ends, a central section generally centered between the distal ends, and a plurality of longitudinally oriented fold lines 70 defining the individual pleats. The accordian style pleat can be provided by a piece of material that is either an extension of the topsheet 28 or of the backsheet 30. Alternatively, the accordian pleat could be formed from a separate piece of material that has one end affixed either directly or indirectly to the core 36, and the other end affixed to the core-facing side 30a of the backsheet 30. An accordion pleat provides the advantage that relatively large Z-direction separation is feasible, without requiring the pleated section of the material to have an excessive lateral width.

The material having the C-fold, accordion style pleat, or other longitudinally oriented pleat 68 may be longitudinally tapered, or, for ease of manufacture, as shown in the drawings, of a longitudinally constant geometry. If longitudinally tapered, the material having the C-fold or accordion style pleat may provide a generally uniform constraint along the entire longitudinal distance between the end edges of the core 36 and backsheet 30 (36d' and 30d', respectively) which are subtended by the pleated material. If a material with a constant geometry pleat is selected, the width of the C-fold or accordion style pleat at the unattached end edges, 36d' and 30d', of the core 36 and backsheet 30 will control the maximum Z-direction separation, and hence decoupling, of the core 36 from the backsheet 30.

The longitudinally oriented pleated material 68 may be of any longitudinal dimension desired, so long as the material 68 can resist Z-directional separation forces and prevent the sanitary napkin 20 from articulating past the intended open position. For instance, the pleated material 68 may be significantly shorter in longitudinal dimension than other components of the sanitary napkin 20, such as the core 36 and the backsheet 30. It is important, however, that the longitudinally oriented pleated material 68 be longitudinally registered with (i.e., approximately the same distance away from the principal transverse centerline $t_1$) that portion of the sanitary napkin 20 at which it is desired to control the Z-direction separation. In other words, if it is desirable to control the separation at the back end edge 24b of the sanitary napkin 20, or at the principal transverse centerline $t_1$, the material having the longitudinally oriented pleat 68 should be respectively positioned adjacent the back end edge 24b and 30d, or near the principal transverse centerline $t_1$ of the sanitary napkin 20. In addition to the single piece of pleated material on each side of the sanitary napkin 20 shown in the drawings, if desired, discrete pieces of material having longitudinally oriented pleats may be provided at both of the locations described above, or at other locations.

Figure 18:
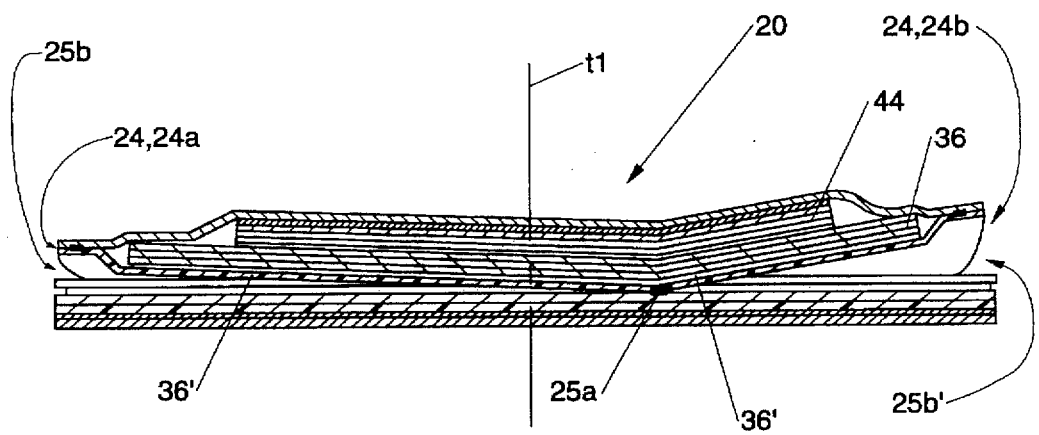

As shown in FIG. 18, the transverse juncture 25a where the core 36 and backsheet 30 are joined need not be coincident with and end 24 of the sanitary napkin 20. As shown in FIG. 18, the transverse juncture 25a may be longitudinally offset inward (i.e., inset) towards the principal transverse centerline $t_1$. If such an embodiment is selected, the transverse juncture 25a should be inset from the end 24 of the sanitary napkin 20 at least about one-fifth of the longitudinal dimension of the sanitary napkin 20. Preferably, the transverse juncture 25a is longitudinally positioned so that the decoupling of the core 36 from the backsheet 30 will conform the sanitary napkin 20 to the wearer's anatomy. Thus, the transverse juncture 25a should be located so that topsheet 28 and core 36 may lift and conform with the wearer's labial tissue in the front portion of the sanitary napkin 20 to more readily intercept menses upon discharge, and the rear portion of the sanitary napkin 20 will lift to fit into the wearer's gluteal groove. A particularly preferred location of the transverse juncture 25a is approximately one-third of the longitudinal distance from either end 24.

As shown in FIG. 18, the arrangement described above provides a sanitary napkin 20 having two unattached end edges 25b and 25b'. The two unattached end edges 25b and 25b' can independently articulate and move in the Z-direction. Thus, the portions of the sanitary napkin 20 (particularly the unattached end edges 25b and 25b') located both in front of and behind the transverse juncture 25a may be separated in the Z-direction.

It will be apparent to one skilled in the art that the transverse juncture 25a, regardless of its longitudinal position, need not be joined across the entire width of the sanitary napkin 20. The core 36 and backsheet 30 may be joined only in the region of the longitudinal edges 36c of the core 36 as illustrated in FIG. 2. In other alternative embodiments, the core 36 may be intermittently joined across the transverse width of the sanitary napkin 20.

If desired, the transverse juncture 25a may be formed by the opposed forces of the body and undergarment against the sanitary napkin 20. This embodiment is more effectively utilized with a relatively tightly fitting undergarment. Such an embodiment (not shown) resembles an open tube and has no transverse juncture 25a where the topsheet 28 and backsheet 30 are joined. If such an embodiment is selected, it should have lesser Z-direction separation than the embodiments described above, otherwise excessive lateral shifting of one component of the sanitary napkin 20 relative to the other components may occur. This lesser separation may be accomplished, for example, by providing longitudinally oriented pleats 68 with a lesser width. A longitudinally oriented pleat 68 having width of about 3 millimeters is suitable for such an embodiment.

Figure 19:
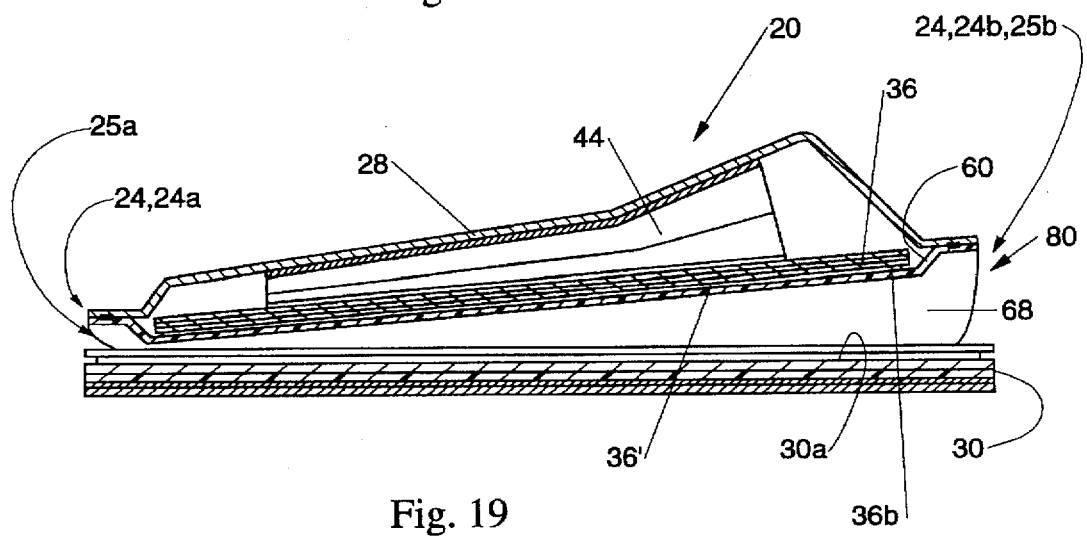

A sanitary napkin 20 according to the present invention may further comprise a transversely-oriented material having a transverse pleat 80 (shown in FIG. 19) that connects the core 36 and the backsheet 30 at the unattached end edge 25b. The material having a transverse pleat is preferably made of a liquid impervious panel that has one end joined to the garment-facing side 36b of the core 36 and one end joined to the core-facing side 30a of the backsheet 30. If desired, the longitudinal edges of the material 80 having the transverse pleat may be joined to the means for controlling the separation of the core 36 and backsheet 30. The material having the transverse pleat 80 provides the advantage that menses which may exceed the absorbent capacity of the core 36 or which migrates longitudinally from or beyond the unattached end edge 25b of the napkin will be retained in the sanitary napkin 20.

Figure 20:
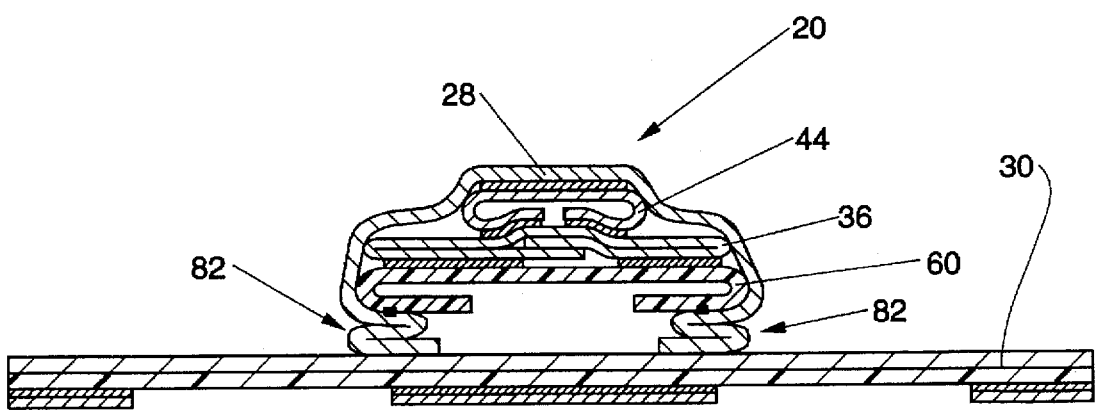

In a less elegant embodiment shown in FIG. 20, the means for controlling the separation of the core 36 from the backsheet 30 of the sanitary napkin 20 may simply comprise flaccid material 82 joining the core 36 to the backsheet 30. As used herein, "flaccid material" refers to material intended to be slack in the Z-direction while the sanitary napkin 20 is in the closed position and allows for movement of such material and associated components in the Z-direction. In such an embodiment, an excess of material of one of the backsheet 30 or topsheet 28 may be joined to the other, or to the core 36 either directly or indirectly. Separation in the Z-direction may occur until the core 36 and the backsheet 30 are restrained from further separating by the flaccid material 82 becoming taut. Such an embodiment is similar to those described above, except the means for controlling the separation of the core 36 and backsheet 30 assumes random, undefined forms, which are not predetermined, when the sanitary napkin 20 is in the closed position. This is in contrast to the aforementioned embodiments where the means for controlling the separation of the core 36 from the backsheet 30 have precise, repeatable and predetermined geometries for both the closed and opened positions.

The amount that the core 36 can separate from the backsheet 30 can vary. For a sanitary napkin 20 having a topsheet 28 longitudinal dimension of between about 13 to about 35 centimeters, the unattached end edges 25b and 25b' should have a maximum separation in the Z-direction of about 1 to about 6 centimeters, and preferably about 3 to 4 centimeters. If the maximum Z-direction separation is less, the desired decoupling of the sanitary napkin 20 components may not occur. This could result in contact not being maintained between the undergarment and the backsheet 30 and between the body of the wearer and the topsheet 28. Conversely, if a greater maximum Z-direction separation occurs at the unattached end edges 25b and 25b ', the sanitary napkin 20 may appear limp and be uncomfortable to wear. Further, a greater Z-direction separation could cause collapsing in the X-Y plane, particularly in the transverse direction, thereby causing the core 36 and backsheet 30 of the sanitary napkin 20 to become misaligned.

In certain embodiments, particularly those where the transverse juncture 25a is at one of the ends 24 of the sanitary napkin 20, the magnitude of the Z-direction separation of the longitudinally centered portion of the sanitary napkin 20 (which is intended to be placed in the proximity of or registered with the vaginal opening), is also important and should be considered. Frequently, the sanitary napkin 20 is isomerically distributed about and longitudinally centered on the vagina of the wearer, (i.e., the principal transverse centerline $t_1$ of the sanitary napkin 20 will be registered with the vagina). If so registered, the Z-direction separation at the principal transverse centerline $t_1$ will be about one-half of the Z-direction separation at the unattached end edge, such as 25b. Thus, the separation at the principal transverse centerline $t_1$ may be from about 0.5 centimeters to about 6 centimeters, and is preferably about 0.5 to 3 centimeters, and more preferably about 1.5 to 2 centimeters.

In addition, if the sanitary napkin 20 has two sets of components that are capable of separating, the separation of the core 36 from the backsheet 30 may be somewhat less than the amounts discussed above when the sanitary napkin 20 is in use. It is believed that in use, the total separation between both sets of components may be in the above ranges. The total separation between both sets of components is limited by the distance between the wearer's body and the wearer's undergarments. When the sanitary napkin 20 is worn, part of the space between the wearer's body and the wearer's undergarments will be occupied by the space created by the separation of the topsheet 28 from the core 36. The remainder will be occupied by the space created by the separation of the core 36 from the backsheet 30.

The amount of separation of the unattached end edges $36d'$ and $30d'$ of the core 36 and backsheet 30 may be measured by the following two methods.

Core/Backsheet Separation Tests

Z-Direction Separation Test

In the first method, the sanitary napkin 20 is attached to a rigid, flat, planar surface in the same manner described above for measuring the separation of the topsheet 28 from the core 36. The core 36, however, is not affixed to the backsheet 30. The intersection of the principal longitudinal centerline $l_1$ and unattached end edge 25b or 25b' of the sanitary napkin 20 is then located. The portion of the core 36 located at this intersection is raised or lifted in the Z-direction until the core 36 is fully articulated from the flat, planar surface and the sanitary napkin 20 is in the open position. The core 36 is lifted from the flat, planar surface by inserting a thin blade (such as a rule or scale about 2.5 centimeters wide and about I millimeter thick) between the core 36 and backsheet 30. The end of the blade is inserted to the transverse juncture 25a. The opposite end of the blade is lifted away from the flat, planar surface while maintaining the inserted end of the blade on the backsheet 30 and adjacent the transverse juncture 25a.

The unattached end edge $36d'$ of the core 36 travels in an arc concavely oriented towards the transverse juncture 25a and the flat, planar surface. The topsheet 28 and core 36 may bow to a slightly concave downward configuration, as the longitudinal center of the core 36 is being raised and the longitudinal edges of the topsheet 28 and core 36 are restrained by the means for controlling the separation of the core 36 from the backsheet 30.

The end of the blade is lifted away from the flat, planar surface until the sanitary napkin 20 is articulated to the open position. When the open position is reached, the Z-direction distance between the core-facing side 30a of the backsheet 30 and the body-facing side 36b of the core 36 is measured in a direction perpendicular to the flat, planar surface. A separate scale, oriented in the Z-direction and generally perpendicular the flat, planar surface, may be used for this measurement. The measurement is taken at the longitudinal position that coincides with the unattached end edges 25b or 25b' of the sanitary napkin 20 when the sanitary napkin 20 is in the open position.

Included Angle Separation Test

Another measure of the desired separation of the core 36 and backsheet 30 is to determine the included angle $\alpha$ which the garment-facing side 36b of the core 36 and the core-facing side 30a of the backsheet 30 define when the sanitary napkin 20 is articulated to the open position.

The measurement of this included angle $\alpha$ may be accomplished in a manner similar to that described above for measuring the amount of Z-direction separation of the core 36 and backsheet 30. The sanitary napkin 20 is affixed, using the means 64 for attaching the sanitary napkin 20 to the undergarment of the wearer, to a rigid flat, planar surface.

The core 36 is articulated to the open position as described above. The amount of Z-direction separation is measured, as described above. The distance taken along the plane of the garment-facing side 36b of the core 36 between the transverse juncture 25a and the unattached end edge 36d along the principal longitudinal centerline $l_1$ is also measured.

The included angle α is then found by triangulating these two measurements. The included angle α is equivalent to the arcsin of the magnitude of the Z-direction separation divided by the distance between the transverse juncture 25a and the unattached edge 36d of the core 36. Preferably the included angle α of the sanitary napkin 26 is between about 3° and about 60°, and more preferably between about 7° and about 20°.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a principal longitudinal centerline, said absorbent article comprising:

a liquid pervious topsheet;

a liquid impervious backsheet joined to said topsheet;

an absorbent core positioned between said topsheet and said backsheet, said absorbent core having two longitudinal edges and a width defined by said longitudinal edges;

said absorbent article having a strip of material positioned between said topsheet and said backsheet and centered along said principal longitudinal centerline, said strip of material having a longitudinal dimension, a transverse dimension, and longitudinal edges, wherein said transverse dimension of said strip of material is less than the width of said absorbent core so that portions of said absorbent core extend outward beyond the longitudinal edges of said strip of material and said absorbent article has a flexure resistance as measured through a first sample of said absorbent article that is taken through said absorbent article outboard of the longitudinal edges of said strip of material and a flexure resistance as measured through a second sample taken through said entire absorbent article containing said strip, said strip of material being relatively stiff so that the flexure resistance of said second sample is greater than the flexure resistance of said first sample, wherein said absorbent article has a caliper of less than about 7 millimeters.

2. A sanitary napkin according to claim 1 wherein a 66.5 cm² sample cut from the portion of the sanitary napkin that would be centered under the vaginal orifice when the sanitary napkin is worn has a test capacity for absorbing sterile saline of at least about 8.0 grams of sterile saline when submerged in sterile saline for 10 minutes and said entire sanitary napkin has a total capacity for absorbing sterile saline of at least about 22.0 grams under the same conditions.

3. The sanitary napkin of claim 2 wherein said strip of material has a length and a width, and the length of said strip of material is between about 2 cm and about 32 cm and the width of said strip of material is between about 20% to about 80% of the width of said absorbent core.

4. The sanitary napkin of claim 2 wherein said strip of material comprises a folded sheet.

5. The sanitary napkin of claim 2 wherein said strip of material is absorbent.

6. The sanitary napkin of claim 2 wherein said strip of material is positioned between said topsheet and said absorbent core.

7. The sanitary napkin of claim 2 wherein said strip of material has a rectangular plan view shape.

8. A sanitary napkin having a principal longitudinal centerline, said sanitary napkin comprising:

a liquid pervious topsheet;

a liquid impervious backsheet joined to said topsheet;

an absorbent core positioned between said topsheet and said backsheet, said absorbent core having two longitudinal edges and a width defined by said longitudinal edges;

said sanitary napkin having a strip of material positioned between said topsheet and said backsheet and centered along said principal longitudinal centerline, said strip of material having a longitudinal dimension, a transverse dimension, and longitudinal edges, wherein said transverse dimension of said strip of material is less than the width of said absorbent core so that portions of said absorbent core extend outward beyond the longitudinal edges of said strip of material and said sanitary napkin has a flexure resistance as measured through a first sample of said sanitary napkin that is taken through said sanitary napkin outboard of the longitudinal edges of said strip of material and a flexure resistance as measured through a second sample taken through said entire sanitary napkin containing said strip of material, said strip of material being relatively stiff so that the flexure resistance of said second sample is greater than the flexure resistance of said first sample, wherein said sanitary napkin has a caliper of less than about 7 millimeters.

* * * * *